US010361073B2

(12) United States Patent
Cooks et al.

(10) Patent No.: US 10,361,073 B2
(45) Date of Patent: Jul. 23, 2019

(54) SYNCHRONIZATION OF ION GENERATION WITH CYCLING OF A DISCONTINUOUS ATMOSPHERIC INTERFACE

(71) Applicant: Purdue Research Foundation, West Lafayette, IN (US)

(72) Inventors: Robert Graham Cooks, West Lafayette, IN (US); Jason Duncan, Dayton, IN (US); Guangming Huang, West Lafayette, IN (US); Guangtao Li, Carmel, IN (US); Xin Yan, West Lafayette, IN (US); Ewa Sokol, West Lafayette, IN (US); Xin Li, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/355,501

(22) Filed: Nov. 18, 2016

(65) Prior Publication Data

US 2017/0084438 A1 Mar. 23, 2017

Related U.S. Application Data

(63) Continuation of application No. 14/052,815, filed on Oct. 14, 2013, now Pat. No. 9,500,623, which is a
(Continued)

(51) Int. Cl.
*H01J 49/04* (2006.01)
*G01N 27/62* (2006.01)
*H01J 49/00* (2006.01)

(52) U.S. Cl.
CPC ............ *H01J 49/045* (2013.01); *G01N 27/62* (2013.01); *H01J 49/0018* (2013.01); *H01J 49/0445* (2013.01); *Y10T 436/24* (2015.01)

(58) Field of Classification Search
None
See application file for complete search history.

(56) References Cited

U.S. PATENT DOCUMENTS 6,107,626 A 8/2000 Wang et al.
7,189,977 B2 3/2007 Yamaguchi et al.
(Continued)

FOREIGN PATENT DOCUMENTS

JP 2002-510052 A 4/2002
WO 2010/127059 A1 11/2010

OTHER PUBLICATIONS

Zhu, L. et al. Real-time, on-line monitoring of organic chemical reactions using extractive electrospray ionization tandem mass spectrometry, 2008, Rapid Communicaitons in Mass Spectrometry, vol. 22, pp. 2993-2998.*
(Continued)

*Primary Examiner* — Xiaoyun R Xu
(74) *Attorney, Agent, or Firm* — Brown Rudnick LLP; Adam M. Schoen

(57) ABSTRACT

The invention generally relates to methods and devices for synchronization of ion generation with cycling of a discontinuous atmospheric interface. In certain embodiments, the invention provides a system for analyzing a sample that includes a mass spectrometry probe that generates sample ions, a discontinuous atmospheric interface, and a mass analyzer, in which the system is configured such that ion formation is synchronized with cycling of the discontinuous atmospheric interface.

20 Claims, 25 Drawing Sheets

Related U.S. Application Data continuation-in-part of application No. 13/887,911, filed on May 6, 2013, now Pat. No. 9,184,036, which is a continuation-in-part of application No. PCT/US2012/021964, filed on Jan. 20, 2012.

(60) Provisional application No. 61/434,473, filed on Jan. 20, 2011.

(56) References Cited

U.S. PATENT DOCUMENTS

| | | | |
|---|---|---|---|
| 7,915,579 | B2 | 3/2011 | Chen et al. |
| 8,330,119 | B2 | 12/2012 | Chen et al. |
| 2005/0199799 | A1 | 9/2005 | Takada et al. |
| 2005/0230635 | A1 | 10/2005 | Takats et al. |
| 2008/0179511 | A1 | 7/2008 | Chen et al. |
| 2010/0301209 | A1 | 12/2010 | Ouyang et al. |
| 2013/0023005 | A1 | 1/2013 | Chen et al. |

OTHER PUBLICATIONS

Miao et.al., Direct Analysis of Liquid Samples by Desorption Electrospray Ionization-Mass Spectrometry (DESI-MS), J Am Soc Mass Spectrom 2009, 20,10-19.

Ferguson et al., Direct Ionization of Large Proteins and Protein Complexes by Desorption Electrospray Ionization-Mass Spectrometry, Anal. Chem. 2011, 83, 6468-6473.

Liu et al., Recent advances of electrochemical mass spectrometry, Analyst, 2013, 138, 5519-5539.

Liu et al., Signal and charge enhancement for protein analysis by liquid chromatography-mass spectrometry with desorption electrospray ionization, International Journal of Mass Spectrometry 325-327 (2012) 161-166.

Lui et al., Measuring Protein?Ligand Interactions Using Liquid Sample Desorption Electrospray Ionization Mass Spectrometry, Anal. Chem. 2013, 85, 11966?11972.

Zhang et al., Paper Spray Ionization of Noncovalent Protein Complexes, Jan. 1, 2014, Anal. Chem. A-E.

Zhang et al., Electrochemistry-Assisted Top-Down Characterization of Disulfide-Containing Proteins, Anal Chem. Apr. 17, 2012; 84(8): 1-7.

Zhang et al., Mass Spectrometric Analysis of Thiol Proteins/Peptides Following Selenamide Derivatization and Electrolytic Reduction of Disulfide Bonds, Dec. 2012, 240 pp.

Peng, et al., "Controlling Charge States of Peptides through Inductive Electrospray Ionization Mass Spectrometry," 2011, Analytical Chemistry, vol. 83, pp. 8863-8866.

Extended EP Search Report dated Oct. 19, 2017 for EP12736853.8.

Gao et al., "Characterization of a discontinuous atmospheric pressure interface. Multiple ion introduction pulses for improved performance," International Journal of Mass Spectrometry, vol. 283, No. 1-3, Jun. 2009.

Gao, et al. "Breaking the Pumping Speed Barrier in Mass Spectrometry: Discontinuous Atmospheric Pressure Interface," Analytical Chemistry, vol. 80. No. 11, Jun. 2008.

Office Action dated Aug. 28, 2017 for JP 2016-195522.

\* cited by examiner

SYNCHRONIZATION OF ION GENERATION WITH CYCLING OF A DISCONTINUOUS ATMOSPHERIC INTERFACE

RELATED APPLICATION

The present application is a continuation of U.S. nonprovisional application Ser. No. 14/052,815, filed Oct. 14, 2013, which is a continuation-in-part of U.S. nonprovisional application Ser. No. 13/887,911, filed May 6, 2013, which is a continuation-in-part of PCT/US12/21964, filed Jan. 20, 2012, which claims the benefit of and priority to U.S. provisional patent application Ser. No. 61/434,473, filed Jan. 20, 2011, the content of each of which is incorporated by reference herein in its entirety.

GOVERNMENT SUPPORT

This invention was made with U.S. government support under N00014-05-1-0454 awarded by U.S. Office of Naval Research and CHE0848650 awarded by National Science Foundation. The U.S. government has certain rights in the invention.

FIELD OF THE INVENTION

The invention generally relates to methods and devices for synchronization of ion generation with cycling of a discontinuous atmospheric interface.

BACKGROUND

Mass spectrometry (MS) plays an important role in chemical analysis which is currently being enhanced by the increasing demand for rapid trace analysis in the areas of public safety, forensics, food safety and pharmaceutical quality assurance, amongst others. These demands have produced a need to simplify MS instrumentation and methodologies. This in turn has resulted in the development of miniaturized instrumentation (Gao et al., Anal. Chem. 2006, 78, 5994-6002; Cotte-Rodriguez et al., Analyst 2006, 131, 579-589; and Cotte-Rodriguez et al., Anal. Chem. 2008, 80, 1512-1519) and development of ambient ionization methods in which samples are examined without preparation in their native state (Venter et al., TrAC, Trends Anal. Chem. 2008, 27, 284-290; Cooks et al., Biopolymers 2009, 92, 297-297; Ifa et al., Analyst 2010, 135, 669-681; Shiea et al., Rapid Commun. Mass Spectrom. 2005, 19, 3701-3704; Huang et al., Annu. Rev. Anal. Chem. 2010, 3, 43-65; Chen et al., J Am Soc Mass Spectrom 2009, 20, 1947-1963; Law et al., Angew. Chem., Int. Ed. 2009, 48, 8277-8280; Chingin et al., Angew. Chem., Int. Ed. 2010, 49, 2358-2361; and Weston, Analyst 2010, 135, 661-668). Particularly, miniaturized instrumentation is being combined with ambient ionization methods to produce mass spectrometers that can be easily used outside of laboratories.

However, a problem with a system that combines miniaturized instrumentation and ambient ionization is that such a system is limited by the low pumping speed of small mass spectrometers and the large nebulizing gas and solvent volumes that must be handled. This problem has been addressed by the development of a discontinuous atmospheric pressure interface (DAPI; Gao et al., Anal. Chem. 2008, 80, 4026-4032; Gao et al., Int. J. Mass Spectrom. 2009, 283, 30-34; and Gao et al., Int. J. Mass Spectrom. 2009, 283, 30-34). The DAPI interface is opened briefly to admit a bolus of ions, solvent vapor and gas, then closed while the neutrals are pumped away before the trapped ions are mass analyzed.

Even with the implementation of a DAPI, there is still a need to increase the sensitivity and sampling efficiency of systems that combine miniaturized instrumentation and ambient ionization.

SUMMARY

The invention recognizes that synchronizing ion generation with cycling of a discontinuous atmospheric interface provides a system with improved sensitivity, reduced solvent usage, reduced nebulizing gas usage, and improved sampling efficiency compared to previous systems in which ion generation is continuous and operates independently of cycling of the discontinuous atmospheric pressure interface. In this manner, systems of the invention provide a more sensitive and more efficient mass spectrometer. Particularly, systems of the invention are well suited for use outside of laboratories and at the location of the sample, e.g., a crime scene, a food processing facility, or a security check-point at an airport.

In certain aspects, the invention provides a system for analyzing a sample that includes a mass spectrometry probe that generates sample ions, a discontinuous atmospheric interface, and a mass analyzer, in which the system is configured such that ion formation is synchronized with cycling of the discontinuous atmospheric interface. In certain embodiments, the probe includes a spray emitter and a high voltage source, in which the probe is configured such that the high voltage source is not in contact with spray emitted by the spray emitter. In certain embodiments, the ions are generated by inductive charging. Such an inductive charging probe is shown herein to be interfaced with a discontinuous atmospheric pressure interface, however, such products can be directed interfaced with any type of mass spectrometer without the use of a discontinuous atmospheric pressure interface.

In other aspects, the invention provides a method for analyzing a sample that involves generating ions of an analyte in a sample using a mass spectrometry probe, discontinuously directing the ions into a mass analyzer, and analyzing the ions, in which the generating step is synchronized with the directing of the ions into the mass analyzer. Discontinuous atmospheric pressure interfaces and methods for discontinuously directing ions into a mass analyzer are described in U.S. Pat. No. 8,304,718, the content of which is incorporated by reference herein in its entirety.

The mass spectrometry probe may be any probe known in the art. In certain embodiments, the probe operates by a direct ambient ionization technique. Exemplary mass spectrometry techniques that utilize direct ambient ionization/sampling methods including desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desoption/ionization (ELDI; Shiea et al., J. Rapid Communications in Mass Spectrometry, 19:3701-3704, 2005). The content of each of these references in incorporated by reference herein its entirety. In particular embodiments, the direct ambient ionization technique is desorption electrospray ionization.

In other embodiments, the probe operates by electrospray ionization. In other embodiments, the probe is a paper spray probe (international patent application number PCT/US10/32881). In other embodiments, the probe is a low temperature plasma probe. Such probes are described in U.S. patent application Ser. No. 12/863,801, the content of which is incorporated by reference herein in its entirety.

In other embodiments, the system further includes a source of nebulizing gas. In certain embodiments, the source of nebulizing gas is configured to provide pulses of gas. Generally, the gas pulses are also synchronized with ion formation and cycling of the discontinuous atmospheric interface.

In certain embodiments, discontinuously directing ions into the mass analyzer may involve opening a valve connected to an atmospheric pressure interface, wherein opening of the valve allows for transfer of ions substantially at atmospheric pressure to the mass analyzer at reduced pressure, and closing the valve connected to the atmospheric pressure interface, wherein closing the valve prevents additional transfer of the ions substantially at atmospheric pressure to the mass analyzer at reduced pressure.

The mass analyzer may be for a mass spectrometer or a miniature or handheld mass spectrometer. Exemplary mass analyzers include a quadrupole ion trap, a rectalinear ion trap, a cylindrical ion trap, a ion cyclotron resonance trap, or an orbitrap. An exemplary miniature mass spectrometer is a handheld rectilinear ion trap mass spectrometer, which is described, for example in Gao et al. (Anal. Chem., 80:7198-7205, 2008), Hou et al. (Anal. Chem., 83:1857-1861, 2011), and Sokol et al. (Int. J. Mass Spectrom., In Press, Corrected Proof, 2011), the content of each of which is incorporated herein by reference herein in its entirety.

Another aspect of the invention provides a method for forming sample ions that involves flowing a sample through a device, pulsing voltage from a source that is not in contact with the flowing sample to inductively interact with the flowing sample, thereby producing sample ions. In certain embodiments, the device is a probe that operates by a direct ambient ionization technique, such as desorption electrospray ionization. In other embodiments, the probe operates by electrospray ionization. In other embodiments, the probe is a paper spray probe. In other embodiments, the probe is a low temperature plasma probe. The probe may be interfaced with a discontinuous atmospheric pressure interface or directly interfaced with an ion analyzing device, such as a mass spectrometer.

Another aspect of the invention provides a method for synchronizing sample ion generation from a mass spectrometry probe with cycling of a discontinuous atmospheric interface, involving generating a sample spray from a mass spectrometry probe, pulsing voltage from a source that is not in contact with the sample spray to inductively interact with the sample spray, thereby producing sample ions, and synchronizing the pulsing of the voltage with the cycling of a discontinuous atmospheric interface. Methods of the invention may further involve pulsing nebulizing gas to interact with the sample, in which the gas pulses are also synchronized with ion formation and cycling of the discontinuous atmospheric interface.

Another aspect of invention provides a method for applying high voltage on electrospray/nanoelectrospray/paper spray tips without physical contact. The induced high voltage leads to burst of droplets in electrospray/nanoelectrospray/paper spray (international patent application number PCT/US10/32881), and the frequency of the spray is that of the applied potential. Methods of the invention may also be used with low temperature plasma probes. Such probes are described in U.S. patent application Ser. No. 12/863,801, the content of which is incorporated by reference herein in its entirety.

Another aspect of the invention provides a method for producing both positive and negative ions in a sample spray that involves applying a pulsed voltage to a sample spray from an electrode that is not in contact with the spray to produce both positive and negative ions in the spray. The method may further involve recording mass spectra of the positive and negative ions. Recording may involve switching polarity of a mass spectrometer while the mass spectrometer is receiving the sample.

BRIEF DESCRIPTION OF THE DRAWINGS

FIG. 1C shows synchronized DESI/DAPI-Mini experiment using 10 ng cocaine. FIG. 1D shows a conventional experiment using 1,000 ng cocaine.

FIG. 3A shows synchronized experiment (80 pL per scan, flow rate 5 nL/min). FIG. 3B shows conventional experiment (6.5 nL, flow rate 400 nL/min). FIG. 3C shows synchronized electrospray MS of 100 ng/mL Ultra mark 1621 recording both polarities in successive scans without any changes in ion source potentials using bench top MS.

FIG. 7A shows an MS detector operating in positive mode with 5 positive pulses high voltage (1.4 kV) pulses applied to conventional nano ESI emitter (solution contact) followed by 9 negative pulses (−1.4 kV), insert: protonated ion of cocaine (m/z 304). FIG. 7B shows an MS detector operating in negative mode with 5 positive pulses high voltage (1.4 kV) applied to conventional nano ESI emitter (solution contact) followed by 9 negative pulses (−1.4 kV), insert: deprotonated ion of p-toluenesulfonic acid (m/z 171).

FIG. 21A is a time range of 0-130 min. FIG. 21B is a time range of 2.5-3.5 min.

DETAILED DESCRIPTION

The invention generally relates to methods and devices for synchronization of ion generation with cycling of a discontinuous atmospheric interface. In certain embodiments, the invention provides a system for analyzing a sample that includes a mass spectrometry probe that generates sample ions, a discontinuous atmospheric interface, and a mass analyzer, in which the system is configured such that ion formation is synchronized with cycling of the discontinuous atmospheric interface. An exemplary system is shown in FIG. 1. The system includes a mass spectrometry probe that operates by an ambient ionization method. Ambient ionization methods include spray-based (Cooks et al., Science 2006, 311, 1566-1570; Takats et al., Science 2004, 306, 471-473; Talaty et al., Analyst 2005, 130, 1624-1633; Liu et al., Anal. Chem. 2010, 82, 2463-2471; Wang et al., Angew. Chem., Int. Ed. 2010, 49, 877-880; Kertesz et al., Anal. Chem. 2008, 80, 1027-1032; Kertesz et al., Anal. Chem. 2008, 80, 5168-5177; and Bereman et al., J. Am. Soc. Mass Spectrom. 2007, 18, 1093-1096) plasma-based (Cody et al., Anal. Chem. 2005, 77, 2297-2302; and Block et al., J. Agric. Food Chem. 2010, 58, 4617-4625) and laser-assisted methods (Brady et al., Rapid Commun. Mass Spectrom. 2010, 24, 1659-1664; Judge et al., Anal. Chem. 2010, 82, 3231-3238; Nemes et al., Anal. Chem. 2007, 79, 8098-8106; Nemes et al., Anal. Chem. 2008, 80, 4575-4582; and Nemes et al., Anal. Chem. 2009, 81, 6668-6675).

Like other ambient methods, desorption electrospray ionization (DESI) has the advantages of simple instrumentation, rapid and sensitive analysis, and broad applicability. Synchronized inductive DESI shows good performance: i) over 100-fold improvement in sensitivity (FIGS. 1c and 1d) while still using the 1:100 DAPI duty cycle, ii) reduced solvent spray flow rate from ~5 µL/min to ~0.5 µL/min, iii) reduced nebulizing gas usage from ca. 2 to 0.2 L/min, iv) improved sampling efficiency by a factor of 100 and v) quasi-simultaneous recording of positive and negative ion spectra using a pulsed monopolar ion source.

FIG. 1 shows a system set-up in which a DESI probe includes a spray emitter and a high voltage source, in which the probe is configured such that the high voltage source is not in contact with spray emitted by the spray emitter. In this manner, the ions are generated by inductive charging, i.e., an inductive method is used to charge the primary microdroplets. This allows droplet creation to be synchronized with the opening of the sample introduction system (and also with the pulsing of the nebulizing gas). The generated ions are directed into the a discontinuous atmospheric interface, a distal end of which is operably coupled to a mass spectrometer. In other embodiments, the inductive probe is directly interfaced with a mass spectrometer and used without a discontinuous atmospheric interface.

Figure 1A:
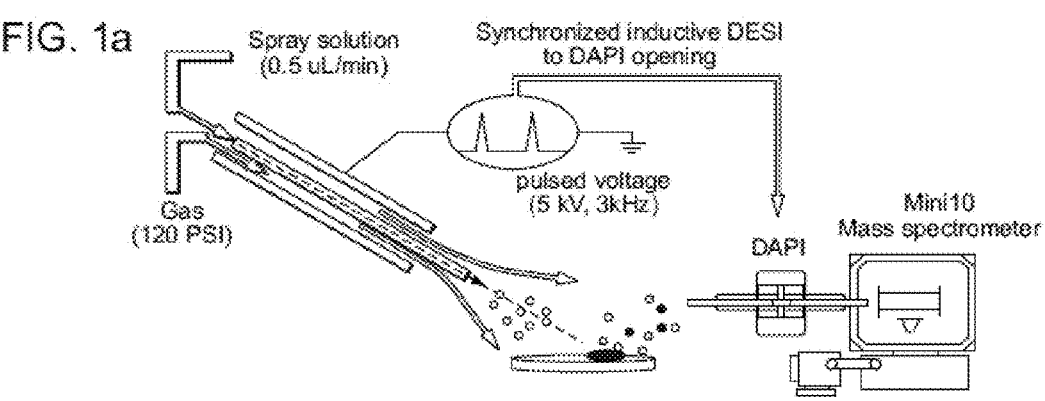
FIG. 1A shows a schematic diagram of system and method of the invention using a miniature MS in which charged droplet creation, nebulizing gas pulsing and sample introduction into the MS are all synchronized.
Figure 1B:
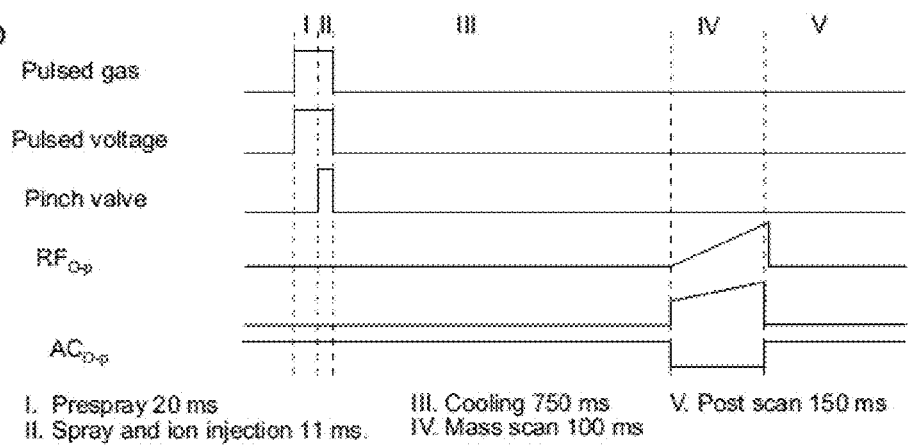
FIG. 1B shows a pulse sequence used in synchronized experiment.
Figure 2A:
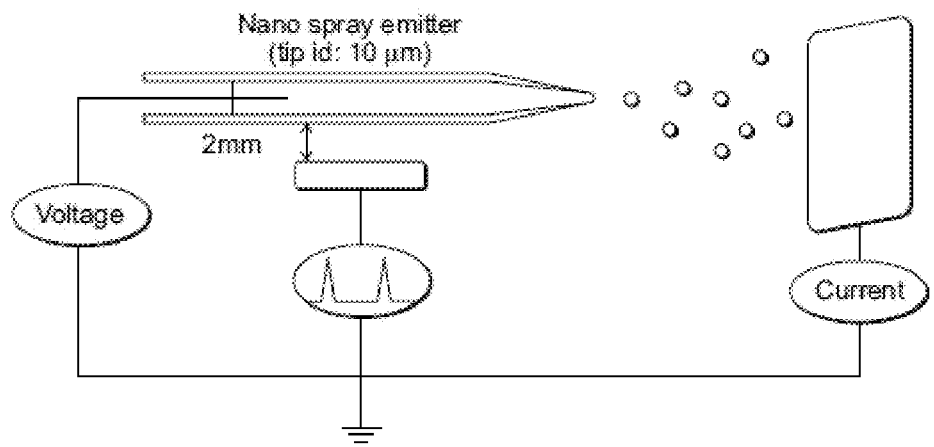
FIG. 2A shows measurement of nano sprayer voltage and current.
Figure 2B:
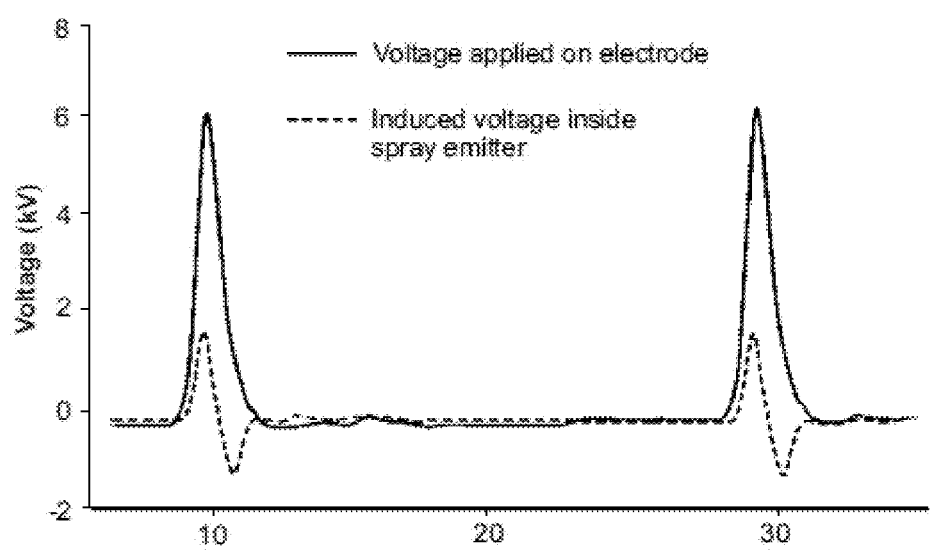
FIG. 2B shows induced voltage recorded inside the DESI source when a nearby electrode voltage is pulsed.
Figure 4:
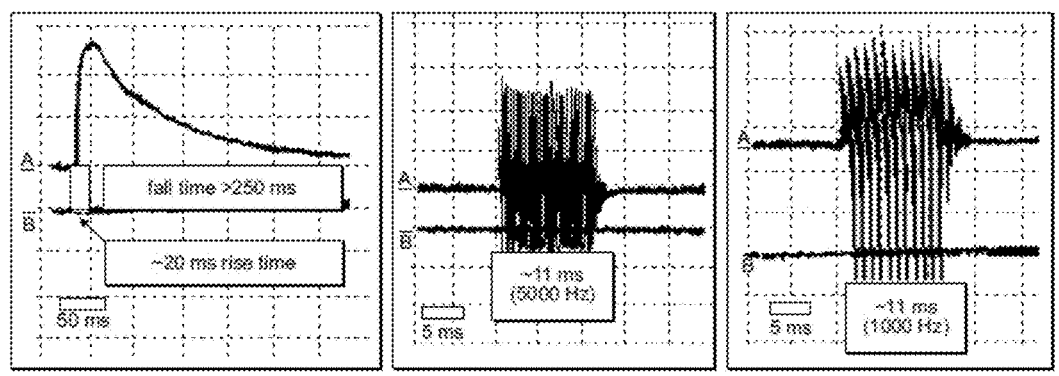
FIG. 4 shows voltage curves measured inside DESI spray emitter tip. Left: single conventional contact DC pulse (3 kV) applied to the solution for 11 msec (rise time ~20 ms, fall time ca. 250 ms). Middle: pulsed inductive DC (5 kV) applied for 11 ms at 5,000 Hz. Right: pulsed inductive DC (5 kV) applied for 11 ms at 1000 Hz. Induced potentials were applied to the outer metal capillary of the DESI source and rise and fall time were less than 1 ms.

Synchronization of ion generation with the cycling of the DAPI is based on accurate control of charged droplet creation by placing an electrode near a spray emitter (typically 2-5 mm distant) and pulsing it repetitively to high positive potentials (5-7 kV, 50-3,000 Hz, pulse width ~0.2-2 ms). The pulsed positive voltage was applied to a metal tube (id 250 μm), covering an inner silica capillary which served as the spray emitter tip (id 50 μm). Electromagnetic induction produces high electrical fields in the DESI source that result in bursts of charged droplets. Precise synchronization with the DAPI interface is possible because the inductive pulsed DC high voltage has the necessary short on/off response times of ca. 1 millisecond (timing control data comparing inductive and conventional contact DC sprays are shown in FIG. 2B and FIG. 4). The nebulizing gas flow was also synchronized to the MS scan function (FIG. 1B). The DAPI pinch valve was opened for the first 10 ms while ions were being admitted into the MS then closed for the remainder of the scan period. Both the spray voltage and nebulizing gas were triggered on 20 ms before the pinch valve was opened, and remained open for the 10 ms during the ion introduction period. The spray solution flow rate was set at 0.5 μL/min. Other DESI conditions in the synchronized experiment remained the same as in the conventional DESI experiment (see Example 1 and Table 1 below).

TABLE 1

Typical synchronized and conventional DESI source settings

|  | Synchronized DESI | conventional DESI |
|---|---|---|
| Spray voltage | 3.5-6 kV [a] | 4-5 kV |
| Solvent flow rate | 0.1-0.5 μL/min | 2-5 μL/min |
| Nebulizing gas flow rate | 0.15 L/min [b] | 2.1 L/min |
| Spray polarity | Provide both positive and negative ions | switchable |
| Angle between source and sample | 40° | 40° |
| Distance between source and sample | 2 mm | 2 mm |
| Distance between sample and MS inlet | 3 mm | 3 mm |
| DAPI opening time | 11 ms | 11 ms |
| Ion production duty cycle | 3% | 100% |
| Ion injection duty cycle | 1% | 1% |

Figure 1C:
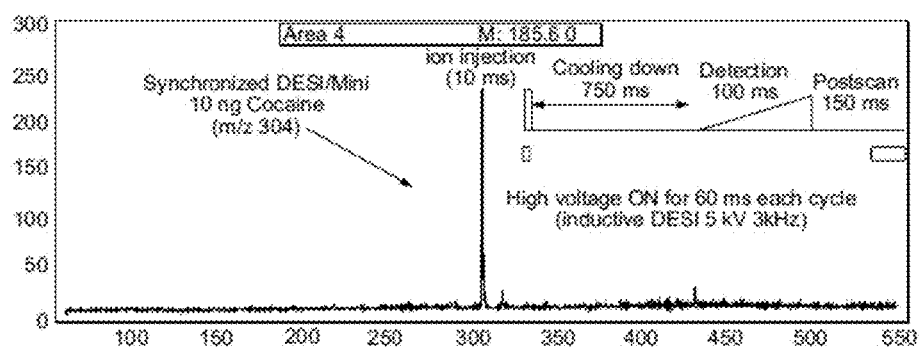
FIGS. 1C-1D show an average of 5 DESI mass spectra recorded for cocaine on a glass substrate, spray solvent MeOH/water (0.5 µL/min) using a mini MS interfaced to a DAPI operated at a duty cycle of 1:100.
Figure 1D:
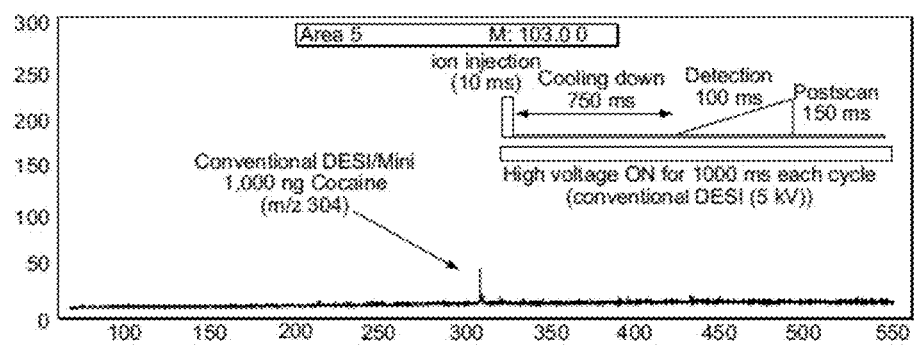
Figure 5:
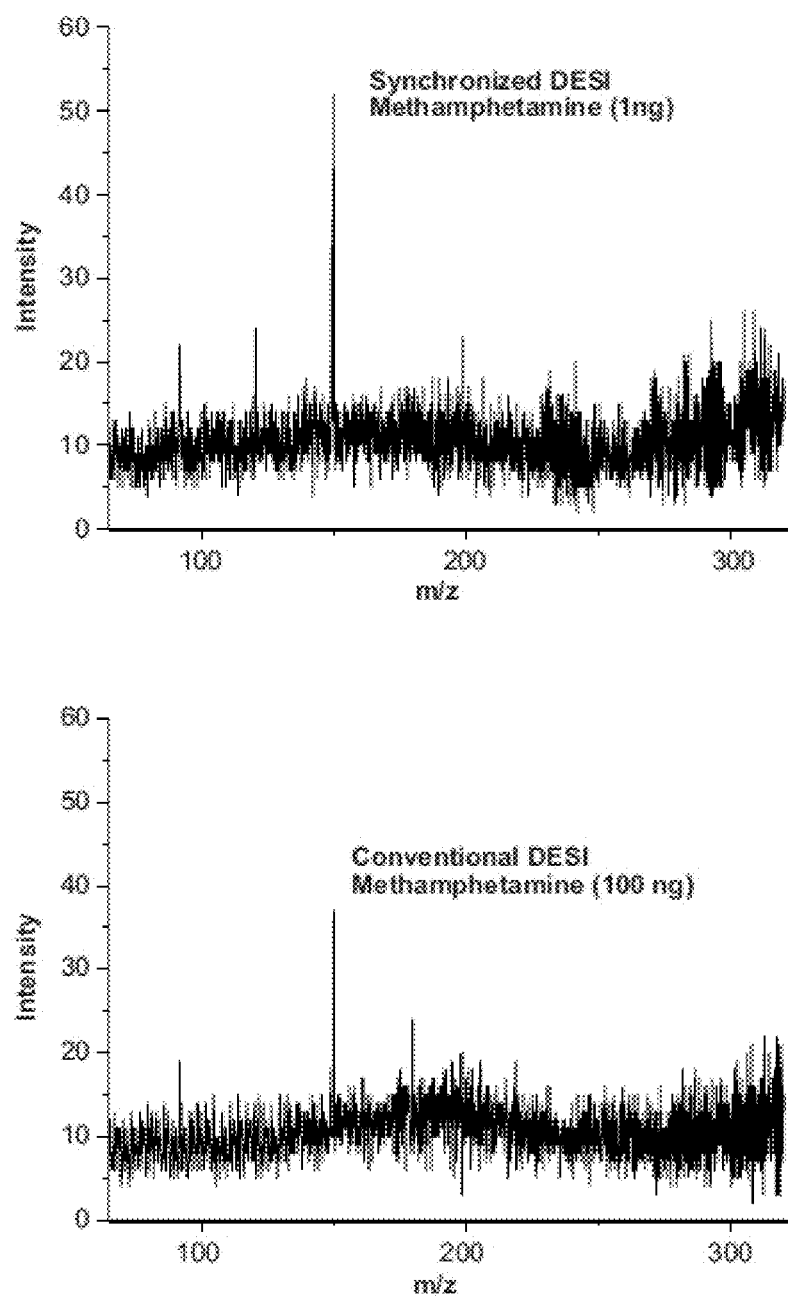
FIG. 5, Top: Synchronized DESI/Mini MS spectrum of 1 ng methamphetamine (m/z 150); Bottom: conventional DESI/Mini MS spectrum of 100 ng methamphetamine (m/z 150).

[a] Inductive voltage measured inside DESI emitter (peak-peak)
[b] Average gas flow rate FIGS. 1C and 1D provide data showing the improved sensitivity and sampling efficiency of systems of the invention compared to conventional ambient ionization systems. FIG. 1C shows that 1 μg of cocaine is needed to record a DESI spectrum in the conventional continuous mode comparable to that given by 10 ng cocaine in the synchronized mode (FIG. 1D). This and similar results for other compounds (atenolol, methamphetamine and morphine) indicate an approximately two orders of magnitude increase in sensitivity for synchronized DESI over conventional DESI using a miniature MS (FIG. 5).

Figure 6:
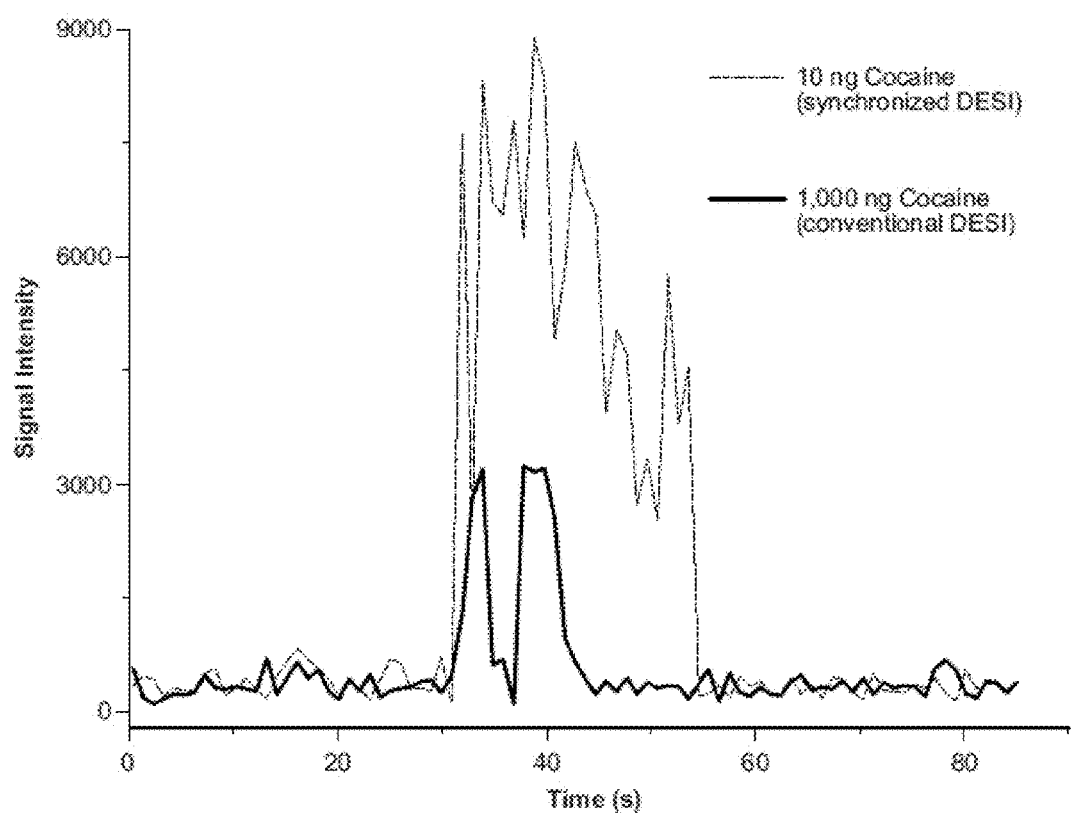
FIG. 6 shows a chronogram of selected ion (m/z 304 for cocaine) using solid curve): 1,000 ng sample which lasts for 15 seconds using conventional DESI/DAPI/Mini 10 and dashed curve): 10 ng sample which lasts for 25 seconds using synchronized DESI/DAPI/Mini 10.

In addition to the decreased detection limits, synchronized DESI also provides higher sampling efficiency. For conventional DESI, 1 μg cocaine signal lasted for ca. 15 seconds, while with synchronization just 10 ng of sample provides signal for the same period (FIG. 6). The improvement of two orders of magnitude in sensitivity is particularly important for samples of small size, where ionization efficiency is most important. Other improvements due to synchronization include the decreased nebulizing gas flow rate from ~2.1 L/min to ~0.15 L/min and the spray solution flow rate decrease from 5 μL/min to 0.5 μL/min.

Figure 2C:
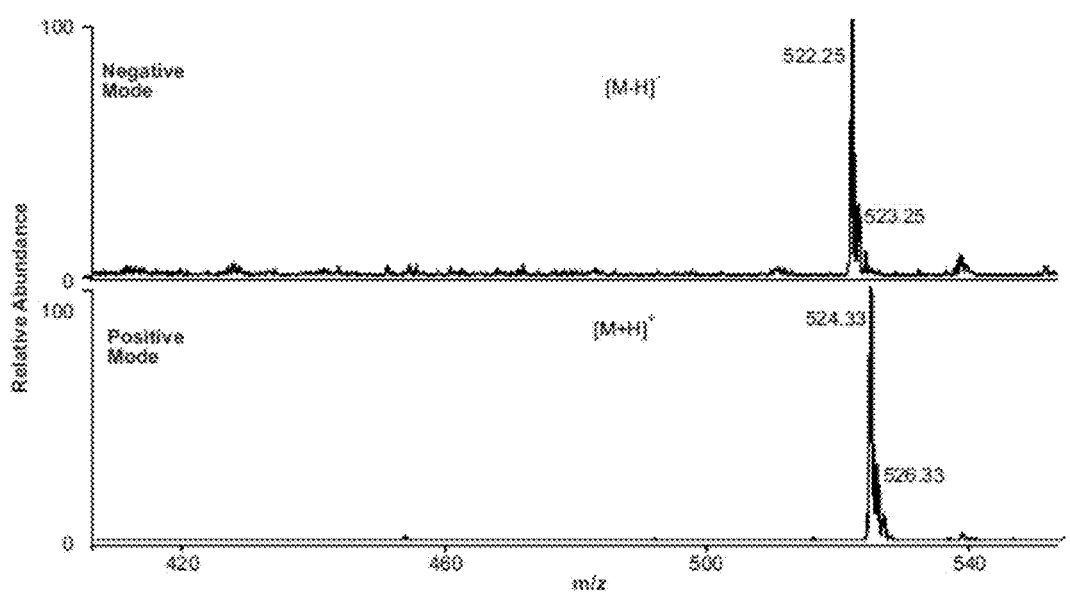
FIG. 2C shows synchronized DESI mass spectra of MRFA (MET-ARG-PHE-ALA) (20 ng on glass) showing both polarities recorded in successive scans made at 5 Hz without changing ion source potentials.
Figure 7:
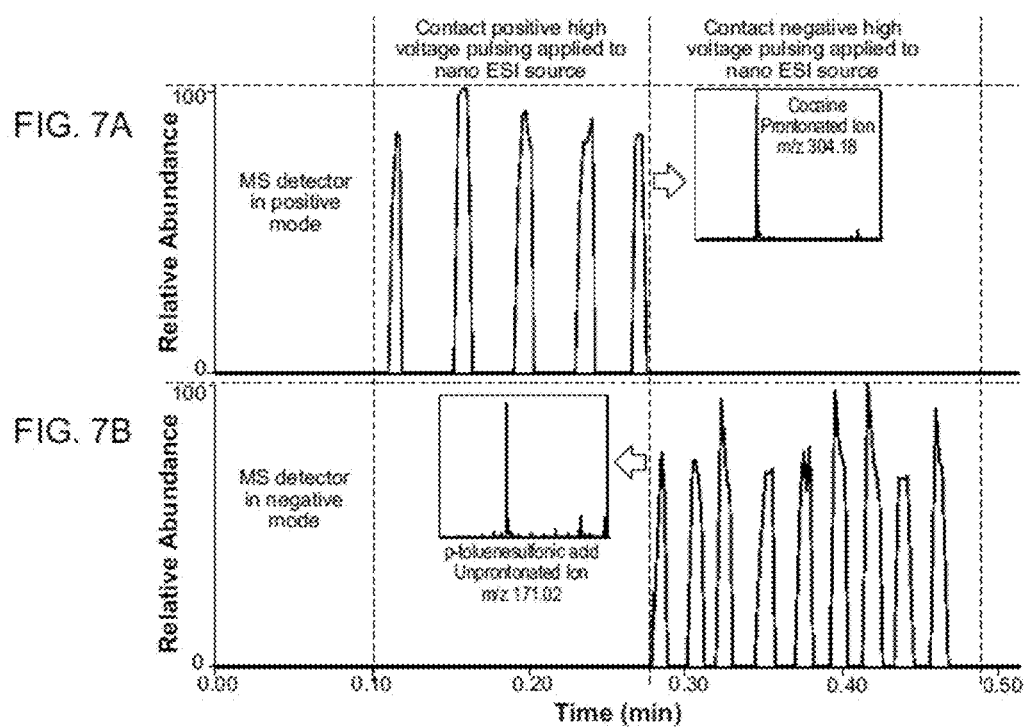
FIGS. 7A-B show total ion chronogram for conventional (contact DC) nano ESI of solution containing both cocaine (300 ng/mL) and p-toluenesulfonic acid (100 ng/mL).

As important as is the improved analytical performance, is the new capabilities achieved in terms of virtually simultaneous production of ions of both positive and negative polarity from a single spray emitter without changing the polarity of the applied potential. This capability is illustrated by the spectrum obtained for the tetrapeptide MRFA (FIG. 2C). The protonated molecule appears in the positive mode and the deprotonated form when the polarity of the detector is switched to negative. Detector switching can be done at 1 Hz, fast enough to record spectra of alternating polarities in successive scans. By contrast, conventional pulsed DC electrospray (Maheshwari et al., Appl. Phys. Lett. 2006, 89. 234103; and Chetwani et al., J. Am. Soc. Mass Spectrom. 2010, 21, 1852-1856) provided ions with either positive or negative, but not both polarities (FIG. 7). This bipolar capability is based on the characteristics of the voltages involved in inductive DESI. The induced potential measured inside the DESI spray emitter during the synchronized experiment was found to have the same frequency as the pulsed voltage applied to the outer electrode of the source and an amplitude of 1.2-2 kV, similar to that used in the normal contact experiments (FIGS. 2A-B). However the induced voltage inside the emitter shows ringing with both positive and negative components and a peak-to-peak voltage of ca. 3 kV. The short pulse width of the repetitively pulsed (5-2,000 Hz) positive potential applied to the outer electrode caused the induced potential to swing from high positive to high negative values in 1 ms. An apparently stable electrospray plume could be observed, indicating that the induced potential is high enough to generate an electrospray, similar to that achieved in a direct contact AC electrospray experiment (Maheshwari et al., Appl. Phys. Lett. 2006, 89. 234103; and Chetwani et al., J. Am. Soc. Mass Spectrom. 2010, 21, 1852-1856). The result is that both positive and negative ions can be observed simply by switching the polarity of the mass spectrometer, without making any ion source changes by rapidly polarizing the spray solution in opposite polarities. These new capabilities should facilitate rapid chemical identification and minimize prior sample manipulation.

Figure 3A:
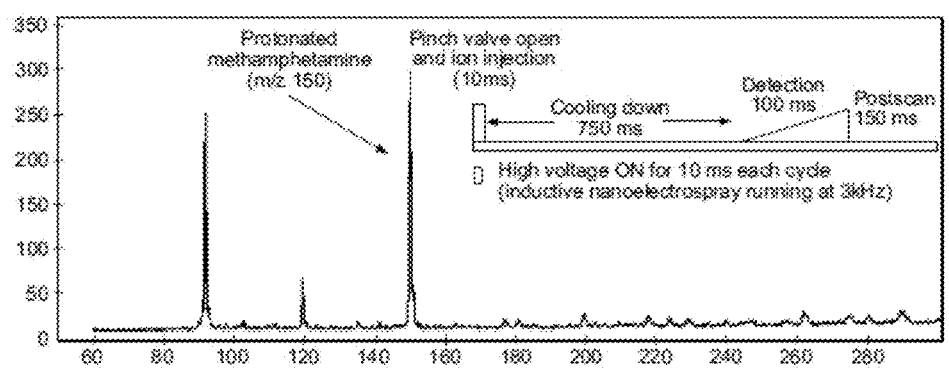
FIGS. 3A-C show nanoelectrospray using 1 µg/mL methamphetamine in MeOH/water with DAPI interface (duty cycle 1:100) on a Mini 10, averaging signal for 5 min.
Figure 3B:
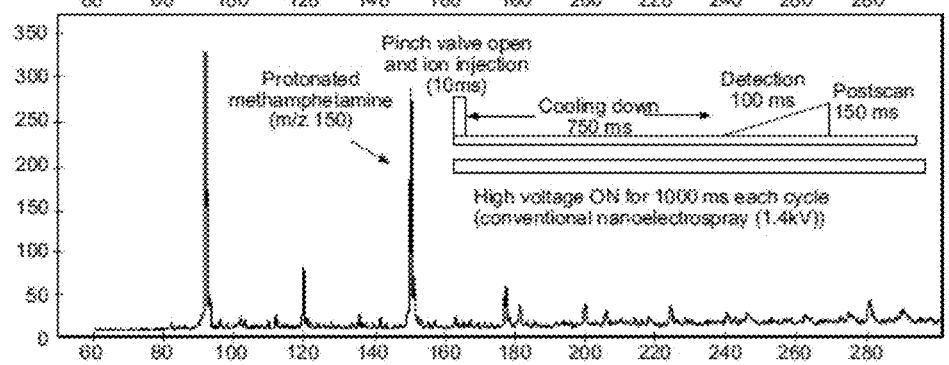
Figure 3C:
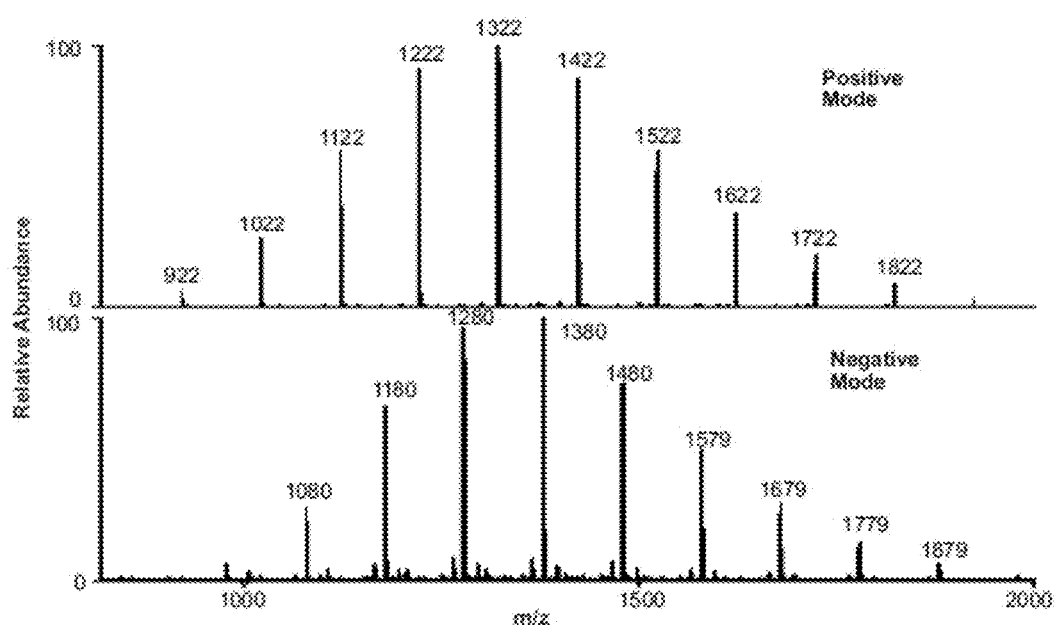
Figure 8:
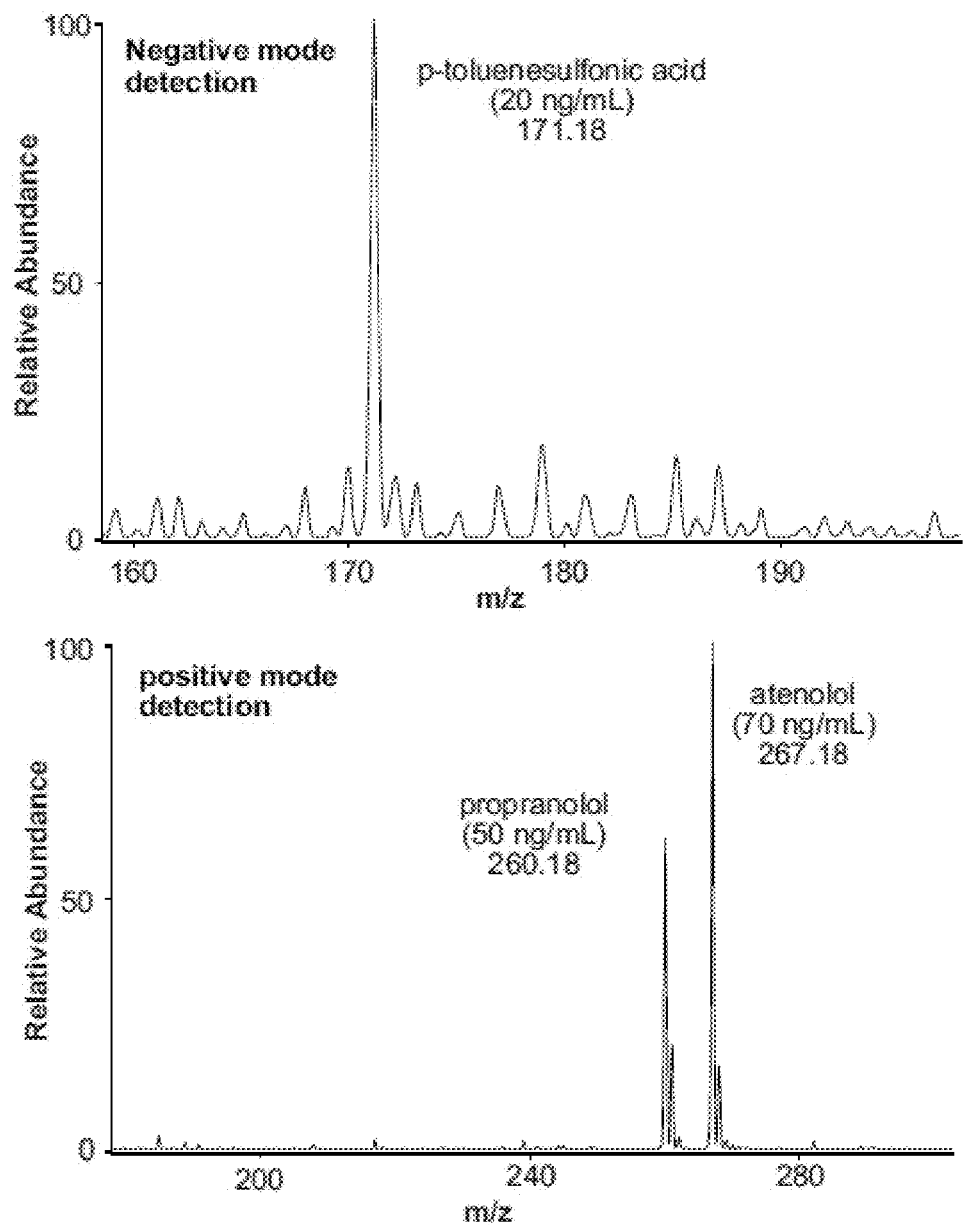
FIG. 8 shows synchronized ESI detection using bench top MS for solution containing p-toluene sulfonic acid (20 ng/mL), propranolol (50 ng/mL) and atenolol (70 ng/mL). Above: spectrum recorded when MS detector operating in negative mode and deprotonated p-toluene sulfonic acid (m/z 171) was detected. Below: spectrum recorded when MS detector operating in positive mode and protonated propranolol (m/z 260) and atenolol (m/z 267) were detected.
Figure 9:
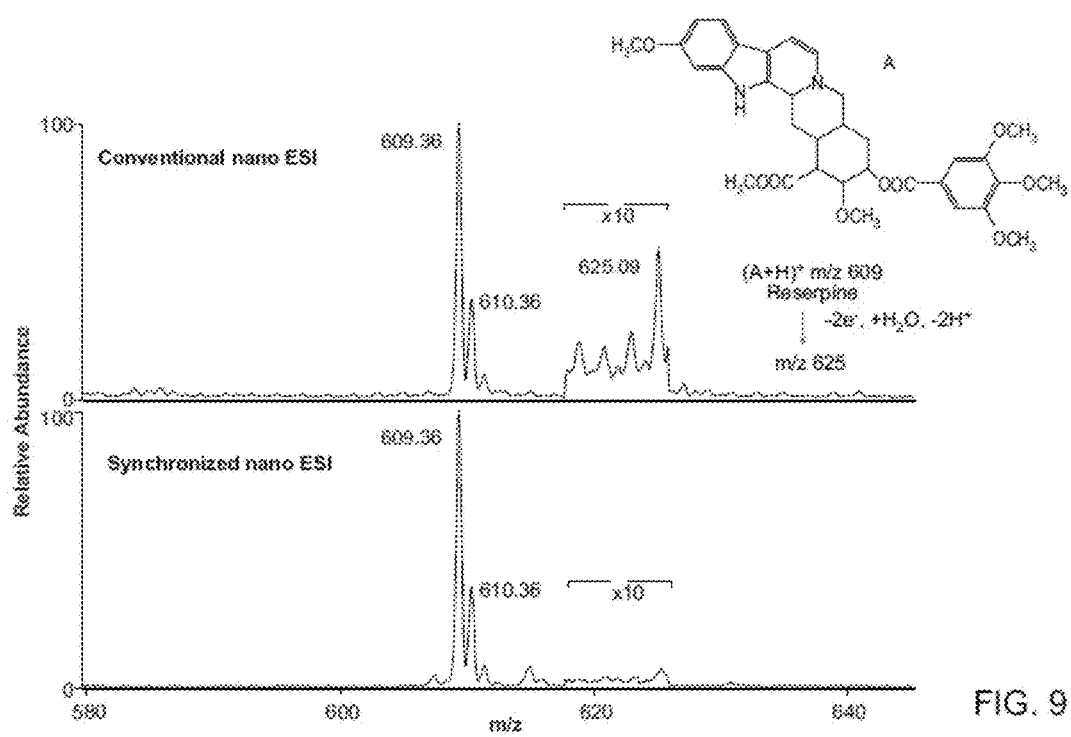
FIG. 9 shows comparison of conventional and synchronized nano ESI MS spectrum of 2 µg/mL reserpine. Top: Conventional nano ESI with oxidization product detected (m/z 625), similar to the results from Peintler-Krivan et al. (Rapid Communications in Mass Spectrometry 2010, 24, 1327-1334). Bottom: Synchronized inductive nano ESI MS spectrum.

FIG. 3 compares the performance of conventional and synchronized nanoelectrospray coupled to a Mini 10. Similar ion intensities and S/N ratios are achieved even though synchronized spray rates are ~80 times lower, corresponding to an 80-fold improvement in sampling efficiency. This highlights an advantage of synchronized ESI or DESI in applications when the sample amount is limited, as in single cell mass spectrometry. The ability to detect ions of both polarities extends to electrospray ionization. Using Ultra mark 1621 (FIG. 3C) as an example, both positive and negative ions can be detected when the synchronized ESI experiment is performed on a commercial benchtop instrument. Similar results were observed for p-toluenesulfonic acid, propranolol and atenolol (FIG. 8). Another advantage of the fast switching of the polarity of the induced potential inside the spray emitter was the elimination of unwanted electrochemical reactions during DESI/ESI (FIG. 9).

In summary, both DESI and ESI benefit in terms of improved sensitivity from controlled droplet generation which is available through the use of induced rather than directly applied potentials (Tu et al., J. Am. Soc. Mass Spectrom. 2008, 19, 1086-1090). These advantages also extend to other ambient ionization methods including plasma-based methods. Synchronization of droplet creation with ion transfer into a miniature mass spectrometer reduces nebulizing gas and solution flow rates by an order of magnitude, and improves in-situ operation. Synchronized DESI also offers significant new capabilities in temporal control of ion polarity on a scan-to-scan basis with millisecond inversion of solution polarity. Recent interest in DESI measurements on the millisecond time scale (Barbula et al., Anal. Chem. 2009, 81, 9035-9040) and in the study of intermediates in solution-phase reactions while sampling on the millisecond time (Perry et al., Angew. Chem., Int. Ed. 2010, in press) might benefit from the bipolarity and enhanced sensitivity of the present methodology.

Discontinuous Atmospheric Pressure Interface (DAPI)

Discontinuous atmospheric interfaces are described in Ouyang et al. (U.S. Pat. No. 8,304,718 and PCT application number PCT/US2008/065245), the content of each of which is incorporated by reference herein in its entirety.

Figure 10:
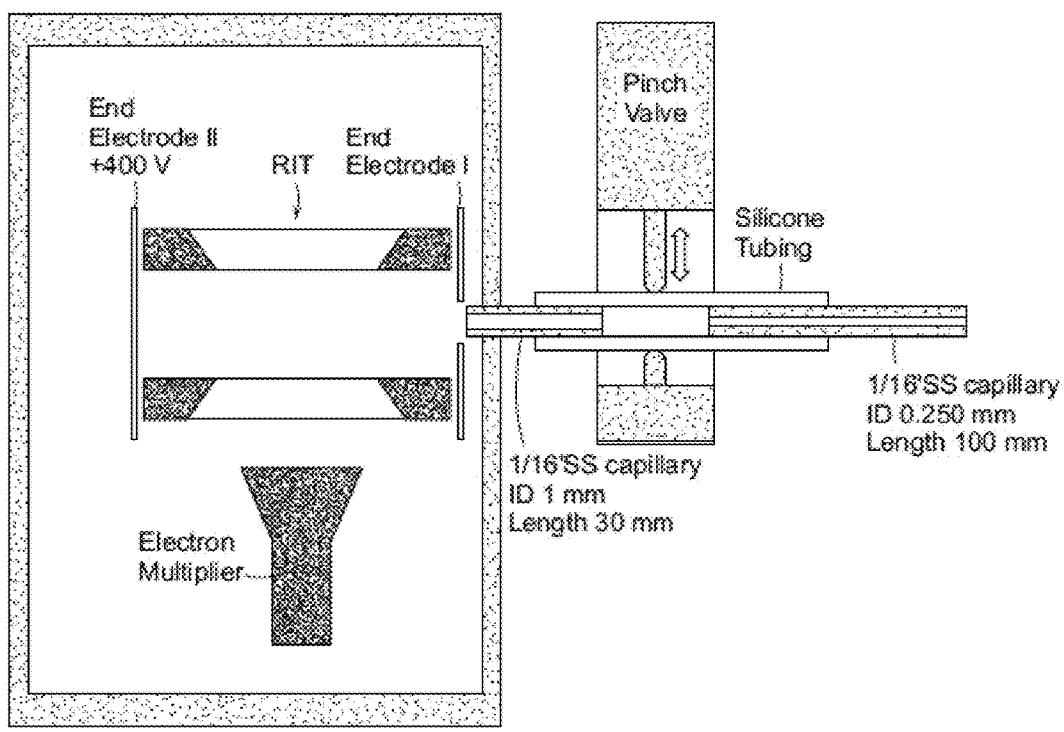
FIG. 10 shows a schematic showing a discontinuous atmospheric pressure interface coupled in a miniature mass spectrometer with rectilinear ion trap.

An exemplary DAPI is shown in FIG. 10. The concept of the DAPI is to open its channel during ion introduction and then close it for subsequent mass analysis during each scan. An ion transfer channel with a much bigger flow conductance can be allowed for a DAPI than for a traditional continuous API. The pressure inside the manifold temporarily increases significantly when the channel is opened for maximum ion introduction. All high voltages can be shut off and only low voltage RF is on for trapping of the ions during this period. After the ion introduction, the channel is closed and the pressure can decrease over a period of time to reach the optimal pressure for further ion manipulation or mass analysis when the high voltages can be is turned on and the RF can be scanned to high voltage for mass analysis.

A DAPI opens and shuts down the airflow in a controlled fashion. The pressure inside the vacuum manifold increases when the API opens and decreases when it closes. The combination of a DAPI with a trapping device, which can be a mass analyzer or an intermediate stage storage device, allows maximum introduction of an ion package into a system with a given pumping capacity.

Much larger openings can be used for the pressure constraining components in the API in the new discontinuous introduction mode. During the short period when the API is opened, the ion trapping device is operated in the trapping mode with a low RF voltage to store the incoming ions; at the same time the high voltages on other components, such as conversion dynode or electron multiplier, are shut off to avoid damage to those device and electronics at the higher pressures. The API can then be closed to allow the pressure inside the manifold to drop back to the optimum value for mass analysis, at which time the ions are mass analyzed in the trap or transferred to another mass analyzer within the vacuum system for mass analysis. This two-pressure mode of operation enabled by operation of the API in a discontinuous fashion maximizes ion introduction as well as optimizing conditions for the mass analysis with a given pumping capacity.

The design goal is to have largest opening while keeping the optimum vacuum pressure for the mass analyzer, which is between 10-3 to 10-10 torr depending the type of mass analyzer. The larger the opening in an atmospheric pressure interface, the higher is the ion current delivered into the vacuum system and hence to the mass analyzer.

An exemplary embodiment of a DAPI is described herein. The DAPI includes a pinch valve that is used to open and shut off a pathway in a silicone tube connecting regions at atmospheric pressure and in vacuum. A normally-closed pinch valve (390NC24330, ASCO Valve Inc., Florham Park, N.J.) is used to control the opening of the vacuum manifold to atmospheric pressure region. Two stainless steel capillaries are connected to the piece of silicone plastic tubing, the open/closed status of which is controlled by the pinch valve. The stainless steel capillary connecting to the atmosphere is the flow restricting element, and has an ID of 250 µm, an OD of 1.6 mm (1/16") and a length of 10 cm. The stainless steel capillary on the vacuum side has an ID of 1.0 mm, an OD of 1.6 mm (1/16") and a length of 5.0 cm. The plastic tubing has an ID of 1/16", an OD of 1/8" and a length of 5.0 cm. Both stainless steel capillaries are grounded. The pumping system of the mini 10 consists of a two-stage diaphragm pump 1091-N84.0-8.99 (KNF Neuberger Inc., Trenton, N.J.) with pumping speed of 5 L/min (0.3 m3/hr) and a TPD011 hybrid turbomolecular pump (Pfeiffer Vacuum Inc., Nashua, N.H.) with a pumping speed of 11 L/s.

When the pinch valve is constantly energized and the plastic tubing is constantly open, the flow conductance is so high that the pressure in vacuum manifold is above 30 torr with the diaphragm pump operating. The ion transfer efficiency was measured to be 0.2%, which is comparable to a lab-scale mass spectrometer with a continuous API. However, under these conditions the TPD 011 turbomolecular pump cannot be turned on. When the pinch valve is de-energized, the plastic tubing is squeezed closed and the turbo pump can then be turned on to pump the manifold to its ultimate pressure in the range of 1×10 5 torr.

The sequence of operations for performing mass analysis using ion traps usually includes, but is not limited to, ion introduction, ion cooling and RF scanning. After the manifold pressure is pumped down initially, a scan function is implemented to switch between open and closed modes for ion introduction and mass analysis. During the ionization time, a 24 V DC is used to energize the pinch valve and the API is open. The potential on the rectilinear ion trap (RIT) end electrode is also set to ground during this period. A minimum response time for the pinch valve is found to be 10 ms and an ionization time between 15 ms and 30 ms is used for the characterization of the discontinuous API. A cooling time between 250 ms to 500 ms is implemented after the API is closed to allow the pressure to decrease and the ions to cool down via collisions with background air molecules. The high voltage on the electron multiplier is then turned on and the RF voltage is scanned for mass analysis. During the operation of the discontinuous API, the pressure change in the manifold can be monitored using the micro pirani vacuum gauge (MKS 925C, MKS Instruments, Inc. Wilmington, Mass.) on Mini 10.

Desorption Electrospray Ionization

Desorption electrospray ionization (DESI) is described for example in Takats et al. (U.S. Pat. No. 7,335,897), the content of which is incorporated by reference herein in its entirety. DESI allows ionizing and desorbing a material (analyte) at atmospheric or reduced pressure under ambient conditions. A DESI system generally includes a device for generating a DESI-active spray by delivering droplets of a liquid into a nebulizing gas. The system also includes a means for directing the DESI-active spray onto a surface. It is understood that the DESI-active spray may, at the point of contact with the surface, include both or either charged and uncharged liquid droplets, gaseous ions, molecules of the nebulizing gas and of the atmosphere in the vicinity. The pneumatically assisted spray is directed onto the surface of a sample material where it interacts with one or more analytes, if present in the sample, and generates desorbed ions of the analyte or analytes. The desorbed ions can be directed to a mass analyzer for mass analysis, to an IMS device for separation by size and measurement of resulting voltage variations, to a flame spectrometer for spectral analysis, or the like.

Figure 11:
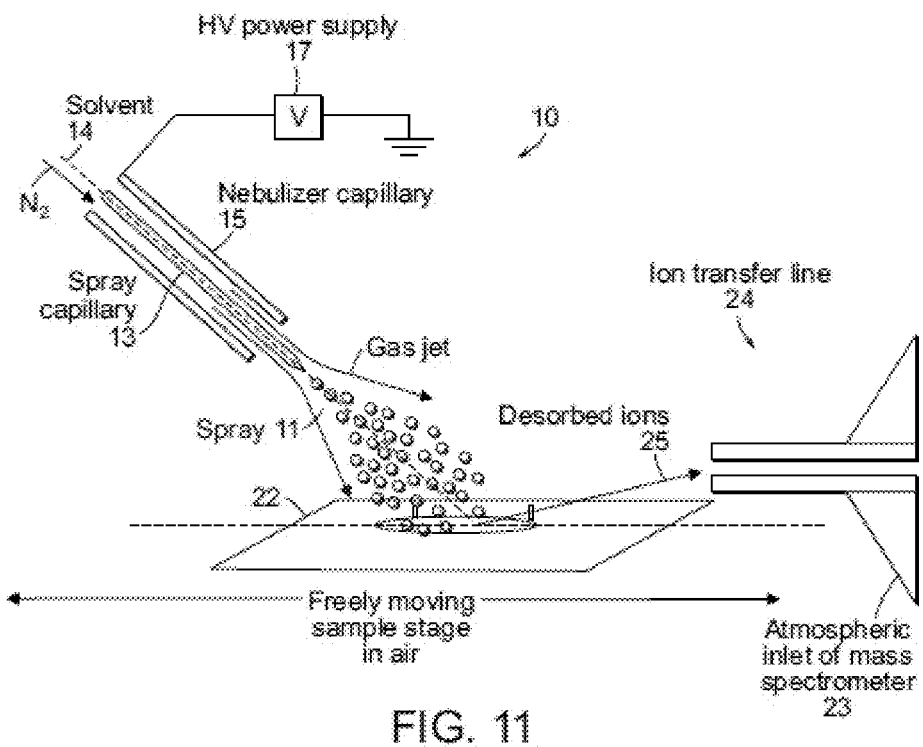
FIG. 11 shows a schematic showing a spray device for generating and directing a DESI-active spray onto sample material (analyte) and for collecting and analyzing the resulting desorbed ions.

FIG. 11 illustrates schematically one embodiment of a DESI system 10. In this system, a spray 11 is generated by a conventional electrospray device 12. The device 12 includes a spray capillary 13 through which the liquid solvent 14 is fed. A surrounding nebulizer capillary 15 forms an annular space through which a nebulizing gas such as nitrogen ($N_2$) is fed at high velocity. In one example, the liquid was a water/methanol mixture and the gas was nitrogen. A high voltage is applied to the liquid solvent by a power supply 17 via a metal connecting element. The result of the fast flowing nebulizing gas interacting with the liquid leaving the capillary 13 is to form the DESI-active spray 11 comprising liquid droplets. DESI-active spray 11 also may include neutral atmospheric molecules, nebulizing gas, and gaseous ions. Although an electrospray device 12 has been described, any device capable of generating a stream of liquid droplets carried by a nebulizing gas jet may be used to form the DESI-active spray 11.

The spray 11 is directed onto the sample material 21 which in this example is supported on a surface 22. The desorbed ions 25 leaving the sample are collected and introduced into the atmospheric inlet or interface 23 of a mass spectrometer for analysis by an ion transfer line 24 which is positioned in sufficiently close proximity to the sample to collect the desorbed ions. Surface 22 may be a moveable platform or may be mounted on a moveable platform that can be moved in the x, y or z directions by well known drive means to desorb and ionize sample 21 at different areas, sometimes to create a map or image of the distribution of constituents of a sample. Electric potential and temperature of the platform may also be controlled by known means. Any atmospheric interface that is normally found in mass spectrometers will be suitable for use in the invention. Good results have been obtained using a typical heated capillary atmospheric interface. Good results also have been obtained using an atmospheric interface that samples via an extended flexible ion transfer line made either of metal or an insulator.

Low Temperature Plasma

Low temperature plasma (LTP) probes are described in Ouyang et al. (U.S. patent application Ser. No. 12/863,801 and PCT application number PCT/US09/33760), the content of each of which is incorporated by reference herein in its entirety. Unlike electrospray or laser based ambient ionization sources, plasma sources do not require an electrospray solvent, auxiliary gases, and lasers. LTP can be characterized as a non-equilibrium plasma having high energy electrons, with relatively low kinetic energy but reactive ions and neutrals; the result is a low temperature ambient plasma that can be used to desorb and ionize analytes from surfaces and produce molecular ions or fragment ions of the analytes. A distinguishing characteristic of the LTP, in comparison with high temperature (equilibrium) plasmas, is that the LTP does not breakdown the molecules into atoms or small molecular fragments, so the molecular information is retained in the ions produced. LTP ionization sources have the potential to be small in size, consume low power and gas (or to use only ambient air) and these advantages can lead to reduced operating costs. In addition to cost savings, LTP based ionization methods have the potential to be utilized with portable mass spectrometers for real-time analytical analysis in the field (Gao, L.; Song, Q.; Patterson, G. E.; Cooks, D. Ouyang, Z., Anal. Chem. 2006, 78, 5994-6002; Mulligan, C. C.; Talaty, N.; Cooks, R. G., Chemical Communications 2006, 1709-1711; and Mulligan, C. C.; Justes, D. R.; Noll, R. J.; Sanders, N. L.; Laughlin, B. C.; Cooks, R. G., The Analyst 2006, 131, 556-567).

Figure 12:
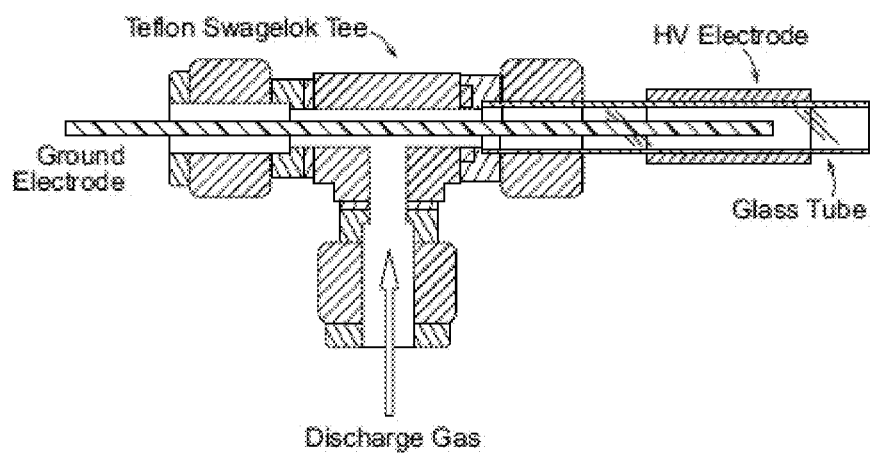
FIG. 12 shows a schematic showing an embodiment of a low temperature plasma (LTP) probe.

An exemplary LTP probe is shown in FIG. 12. Such a probe may include a housing having a discharge gas inlet port, a probe tip, two electrodes, and a dielectric barrier, in which the two electrodes are separated by the dielectric barrier, and in which application of voltage from a power supply generates an electric field and a low temperature plasma, in which the electric field, or gas flow, or both, propel the low temperature plasma out of the probe tip. The ionization source of the probe described herein is based upon a dielectric barrier discharge (DBD; Kogelschatz, U., Plasma Chemistry and Plasma Processing 2003, 23, 1-46). Dielectric barrier discharge is achieved by applying a high voltage signal, for example an alternating current, between two electrodes separated by a dielectric barrier. A non-thermal, low power, plasma is created between the two electrodes, with the dielectric limiting the displacement current. This plasma contains reactive ions, electrons, radicals, excited neutrals, and metastable species in the ambient environment of the sample which can be used to desorb/ionize molecules from a solid sample surface as well as ionizing liquids and gases. The plasma can be extracted from the discharge region and directed toward the sample surface with the force by electric field, or the combined force of the electric field and gas flow.

In certain embodiments, the probe further includes a power supply. The power supply can provide direct current or alternating current. In certain embodiments, the power supply provides an alternating current. In certain embodiments, a discharge gas is supplied to the probe through the discharge gas inlet port, and the electric field and/or the discharge gas propel the low temperature plasma out of the probe tip. The discharge gas can be any gas. Exemplary discharge gases include helium, compressed or ambient air, nitrogen, and argon. In certain embodiments, the dielectric barrier is composed of an electrically insulating material. Exemplary electrically insulating materials include glass, quartz, ceramics and polymers. In other embodiments, the dielectric barrier is a glass tube that is open at each end. In other embodiments, varying the electric field adjusts the energy and fragmentation degree of ions generated from the analytes in a sample.

Ionization Using Wetted Porous Material

Figure 13A:
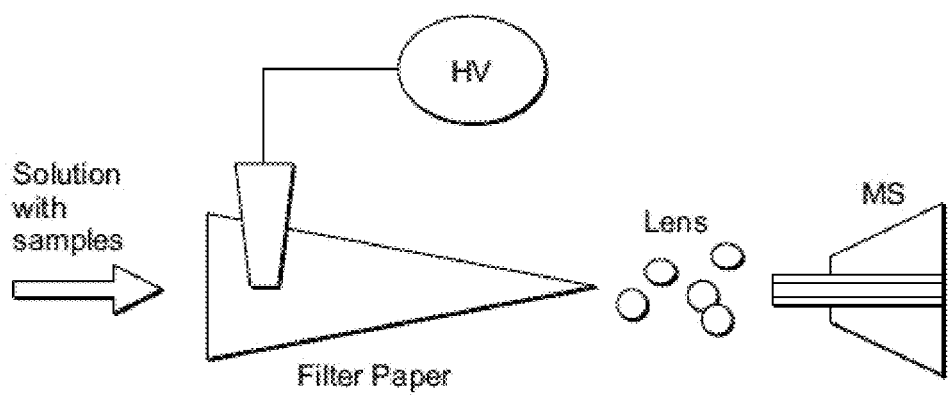
FIG. 13A shows a schematic of a sample solution being fed to a piece of paper for electrospray ionization.
Figure 13B:
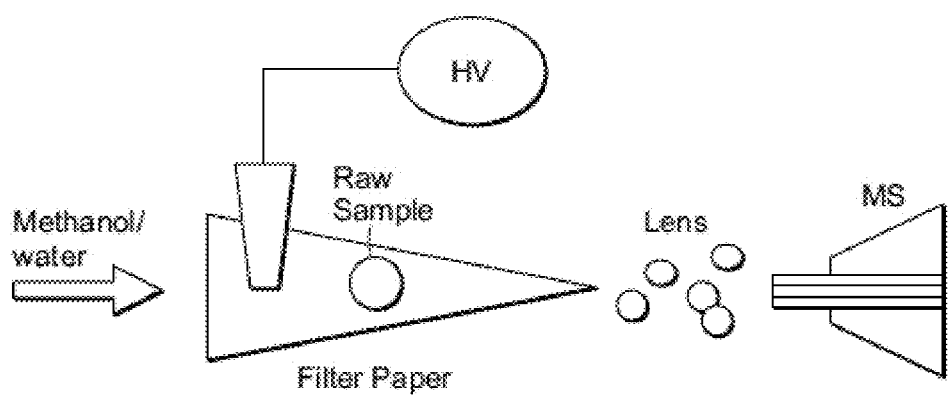
FIG. 13B shows a schematic of a sample solution pre-spotted onto the paper and a droplet of solvent being subsequently supplied to the paper for electrospray ionization.
Figure 14A:
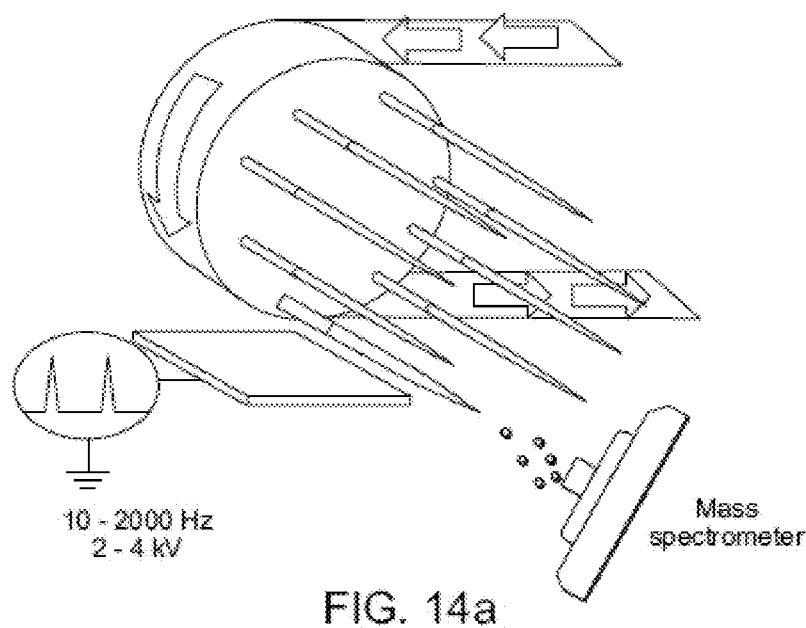
FIG. 14A shows a schematic of high throughput inductive nESI ion source array (rotating form).
Figure 14B:
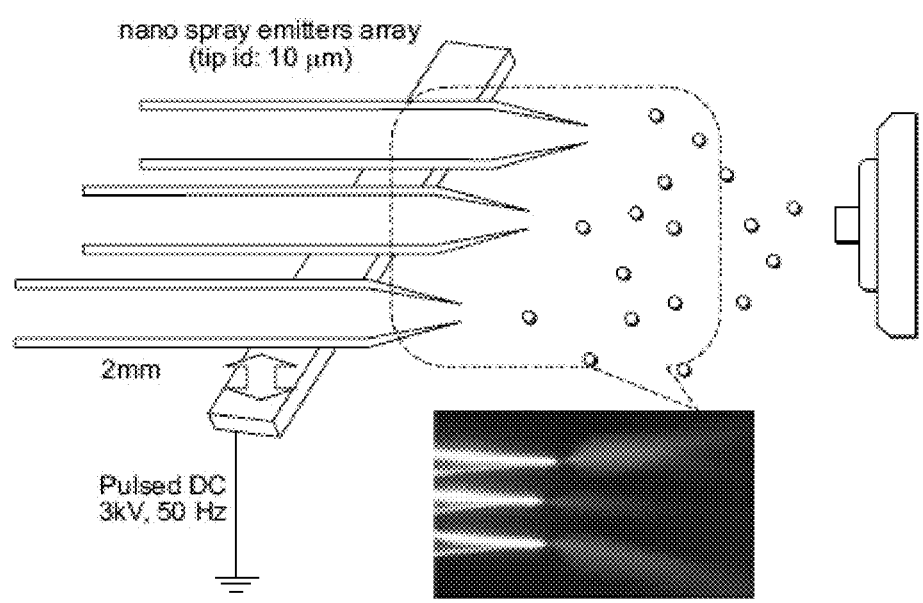
FIG. 14B shows inductive nESI ion source array (linear form), Insert: image of the inductive nESI plume. Applied voltage pulse train (10-3000 Hz, 2-4 kV).

Probes comprised of porous material that is wetted to produce ions are described in Ouyang et al. (U.S. patent application Ser. No. 13/265,110 and PCT application number PCT/US10/32881), the content of each of which is incorporated by reference herein in its entirety. Exemplary probes are shown in FIGS. 13A-B. Porous materials, such as paper (e.g. filter paper or chromatographic paper) or other similar materials are used to hold and transfer liquids and solids, and ions are generated directly from the edges of the material when a high electric voltage is applied to the material. The porous material is kept discrete (i.e., separate or disconnected) from a flow of solvent, such as a continuous flow of solvent. Instead, sample is either spotted onto the porous material or swabbed onto it from a surface including the sample. The spotted or swabbed sample is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 µm), Grade 2 (8 µm), Grade 595 (4-7 µm), and Grade 6 (3 µm). Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultra filtration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 µm or wider, at least about 10 µm or wider, at least about 50 µm or wider, at least about 150 µm or wider, at least about 250 µm or wider, at least about 350 µm or wider, at least about 400µ or wider, at least about 450 µm or wider, etc. In particular embodiments, the tip width is at least 350 µm or wider. In other embodiments, the probe tip width is about 400 µm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples. Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples. In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper.

In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds. Hydrophobic regions may be patterned onto paper by using photolithography, printing methods or plasma treatment to define hydrophilic channels with lateral features of 200~1000 µm. See Martinez et al. (Angew. Chem. Int. Ed. 2007, 46, 1318-1320); Martinez et al. (Proc. Natl Acad. Sci. USA 2008, 105, 19606-19611); Abe et al. (Anal. Chem. 2008, 80, 6928-6934); Bruzewicz et al. (Anal. Chem. 2008, 80, 3387-3392); Martinez et al. (Lab Chip 2008, 8, 2146-2150); and Li et al. (Anal. Chem. 2008, 80, 9131-9134), the content of each of which is incorporated by reference herein in its entirety. Liquid samples loaded onto such a paper-based device can travel along the hydrophilic channels driven by capillary action.

Nano ESI (nESI)

Inductive nESI can be implemented for various kinds of nESI arrays due to the lack of physical contact. Examples of circular and linear modes are illustrated in FIG. 13. In the rotating array, an electrode placed ~2 mm from each of the spray emitters in turn was supplied with a 2-4 kV positive pulse (10-3000 Hz) giving a sequence of ion signals. Simultaneous ions signals were generated in the linear array using pulsed voltages generated inductively in the adjacent nESI emitters. Nanoelectrospray spray plumes were observed and analytes are detected in the mass spectrum, in both positive and negative detection modes.

INCORPORATION BY REFERENCE

Any and all references and citations to other documents, such as patents, patent applications, patent publications, journals, books, papers, web contents, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1: Materials and Methods

Experiments were carried out using a custom built miniature mass spectrometer (Mini 10; Gao et al., Anal. Chem. 2006, 78, 5994-6002) or a Thermo LTQ mass spectrometer (Thermo Scientific, San Jose, Calif.). Capillary temperature: 150° C.; capillary voltage: 15 V; tube lens voltage: 240 V. A custom power supply provided a pulsed output of 50-5,000 Hz and 0-8 kV. DESI (Takats et al., Science 2004, 306, 471-473) conditions were: nitrogen gas 150 psi, a metal tube (id 250 µm, 5 cm long) serves as outer electrode, an inner silica capillary serves as the spray emitter (id 50 µm), angle of DESI sprayer to substrate set at 40°, distance between spray tip and sample set at 2 mm, distance between sample and MS inlet, 3 mm; the spray solution was MeOH/water (v:v=1:1), Commercial silica nanoelectrospray tips of 20 µm were obtained from New Objective (Woburn, Mass., USA).

Example 2: On-Line Reaction Monitoring

Reaction monitoring using MS is of interest because of its chemical specificity, sensitivity and speed. There are many available ambient ionization methods and there have been various attempts to use them for on-line reaction monitoring. Those systems exhibit weaknesses, such as only being capable of off-line monitoring, which becomes ineffective when fast reaction kinetics and short-lived reaction intermediates are involved, having practical drawbacks including severe capillary blockage when used for on-line monitoring of samples even with modestly high concentrations of salts, and system set-ups that are all open-to-air, meaning that reactions sensitive to air/moisture are not currently continuously monitored by MS.

This example shows an on-line reaction monitoring system using inductive electrospray ionization mass spectrometry (MS) to continuously monitor reacting chemical and biochemical systems to detect disappearance of reagents and formation of products and to characterize the transient reaction intermediates. A specific embodiment used a sealed three-neck vessel in which the reaction solution was pressurized by inert gas to allow transfer continuously through a capillary to an emitter-spray tip. Ionization is produced by inductive electrospray ionization, as described throughout. A positive electrospray potential applied to an electrode near to but not in physical contact with the solution being sprayed or the emitter is pulsed repeatedly to produce strong electric fields of both polarities which result in bursts of charged droplets being emitted from the solution while avoiding direct physical contact between the high voltage and the reaction solution. Sheath gas was used to help in the nebulization process and minimize size-variation in the droplets. Sample splitting was useful in accelerating the flow rate of sampling and decreasing the delay time while avoiding contamination of the MS inlet. Mass spectra recorded as a function of time gave the desired kinetic information.

The inductive ESI-MS based monitoring system was used in real-time reaction monitoring, which is critical in process control to assure quality and purity in the manufacture of chemicals materials and pharmaceuticals. Monitoring precursors, intermediates and products during the reaction allows early detection of problems and overall product quality and facilitates yield improvement. Equally important is the fact that the detailed information acquiring during on-line reaction monitoring can help in optimizing reaction conditions and in elucidating reaction mechanisms.

The inductive version of electrospray ionization mass spectrometry (inductive ESI-MS) was explored as a fast and simple way to monitor chemical reactions occurring in complex mixtures in real time. The reactions chosen for study were the reductive amination of 4-pyridine-carboxaldehyde with 4-(aminomethyl)pyridine, and Pd—C catalyzed hydrogenolysis of 3,4-dimethoxy-benzaldehyde. In inductive ESI, a positive electrospray potential is pulsed repeatedly to produce strong electric fields of both polarities which result in bursts of charged droplets being emitted from the solution while avoiding direct physical contact between the high voltage and the reaction solution. The delay time between sampling and analysis was reduced to several seconds using a sample splitter while avoiding contamination of the MS inlet by spraying too large a volume of concentrated reaction solution. Kinetic data obtained by continuous inductive ESI-MS measurements of the reductive amination reaction were verified by intermittent proton NMR. Three short-lived intermediates were observed in the hydrogenolysis reaction, revealing a new triple intermediates pathway for the hydrogenolysis in methanol.

Introduction

Reaction monitoring is critical in process control to assure quality and purity in the manufacture of chemicals and pharmaceuticals. Monitoring precursors, intermediates and products during the reaction allows early detection of problems and overall product quality and yields improvement. Equally important is the fact that the detailed information acquiring during on-line reaction monitoring can help in optimizing reaction conditions and in elucidating reaction mechanisms. Modern methods follow reaction progress by observing spectroscopic and electrochemical methods, even though they have limited capabilities for structure elucidation of products and intermediates present in complex mixtures.

Mass spectrometry (MS) coupled with various ionization methods is of current interest in monitoring reaction because of its structure characterization capability, high specificity and speed. Reaction monitoring using MS involves sampling from the reaction system, ionizing and analyzing the mixture. Based on whether intermittent or continuous sampling is used, monitoring can be divided into off-line and on-line versions with the latter being far more useful and more demanding. Off-line MS reaction monitoring has been done using a variety of ionization methods, electrospray ionization (ESI), matrix-assisted laser desorption/ionization (MALDI), and direct analysis in real time (DART). This approach is useful for kinetic studies of slow reactions as well as providing information on long-lived reaction intermediates. However, it becomes ineffective when fast reaction kinetics and short-lived reaction intermediates are involved. By contrast, on-line MS monitoring does apply in these circumstances but is much more difficult to implement. An aliquot of reaction solution must be continuously transferred from the reaction vessel to the MS for real-time analysis. Manual transfer of samples from the reaction system, as commonly done in off-line reaction monitoring, is completely eliminated. As a result, on-line MS monitoring must allow acquisition of real-time information on the reaction system and intercept and characterize short-lived intermediates. Various ion sources have been investigated for this purpose including ESI, electrospray-assisted laser desorption/ionization (ELDI), ultrasound-assisted spray ionization (USI), extractive electrospray ionization (EESI), and low temperature plasma (LTP) ionization. However, severe limitations have been identified in every case. High-salt-containing sample solutions cannot be handled in conventional ESI sources, due to the likelihood of clogging of the ESI capillary. Heated columns used to vaporize the solution in EESI might expedite the reaction or lead to side products due to the higher temperature. The open-to-air setup of USI and LTP results in evaporation of reaction solvent to the air and completely eliminates applications to air-sensitive or water-sensitive reactions. Substantial previous efforts in this lab using DESI and ESI-based methods for reaction monitoring have had limited success for these reasons.

In inductive electrospray ionization, a potential is applied to a single electrode placed close to the capillary containing the reaction solution. It pulses repeatedly in either the positive or negative mode at a frequency ranging from 10-2000 Hz. Strong dynamic electromagnetic fields are produced in the ESI emitter resulting in a burst of charged droplets. The inductive ESI method is a variant of ESI but provides several new capabilities, such as being characterized by a remarkable tolerance to matrix effects and has a high efficiency. In conventional ESI source, clogging of the ESI capillary occurs quickly when a high-salt-containing sample is sprayed. By contrast, inductive ESI shows a remarkable resistance to deleterious effects of high salt concentrations so much so that even urine and serum samples can be analyzed directly. Inductive ESI uses a mono-polar applied potential and should also not be confused with alternating current (AC) electrospray, which uses an alternating and directly applied potential.

AC electrospray has definite advantages but they do not extend to the remote application of the potential, the control of droplet creation or the immunity to salts and complex matrices seen in inductive ESI. Because inductive ESI avoids physical contact between the electrode and the spray solvent, there is no interference with reaction monitoring. Here, we describe the application of inductive ESI-MS to on-line reaction monitoring. The reaction solution was transferred to the emitter-spray tip by a capillary under positive helium pressure (or other gas) and ionized by applying inductively a pulsed DC voltage. Sheath gas was used to aid in the nebulization process and to minimize variation in the droplet size. To allow rapid monitoring the delay time was reduced to a few seconds by adding a sample splitter, which expedited sample transfer and prevented solution contamination of the MS inlet. Two reactions important in drug synthesis were selected for monitoring: (1) reductive amination of 4-pyridine-carboxaldehyde with 4-(aminomethyl) pyridine (Scheme 1a), and (2) Pd—C catalyzed hydrogenolysis of 3,4-dimethoxy-benzaldehyde (Scheme 1b).

reaction vessel pressure and exclude atmospheric oxygen and water from the reaction. A tee was added at the very front of the capillary tip to allow sheath gas to aid in the nebulization process and minimize size-variation in the droplets. Without the sheath gas, the signal was as much as 100 times poorer and more erratic. A three-way sample splitter was added right after the sheath gas tee. An 8 cm long fused silica capillary, i.d. 100 µm, was connected through the sheath gas tee. The other outlet of the splitter was linked to a fused silica capillary, i.d. 200 µm, length 8 cm. A home-built power supply provided a positive pulsed output of 2000 Hz on the sheath gas. Strong electric fields were produced in the solution inside the emitter to give a burst of droplets. This procedure resulted in the pulsed emission of charged analytes from the reaction solution at a controlled pulse rate. The spray was directed towards the inlet of the MS which was ca. 5 mm from the capillary tip.

Mass Spectrometry

A linear ion trap mass spectrometer (LTQ, Thermo Fisher Scientific, San Jose, Calif., USA) was used to record positive ion mode mass spectra. Typical MS parameters used included averaging of 3 microscans, 100 ms maximum injection time, 15 V capillary voltages, 150° C. capillary temperature, and 65 V tube lens voltage. Data were acquired and processed using Xcalibur 2.0 software (Thermo Fisher Scientific, San Jose, Calif., USA). The identification of analyte ions was confirmed by tandem mass spectrometry (MS/MS) using collision-induced dissociation (CID). An

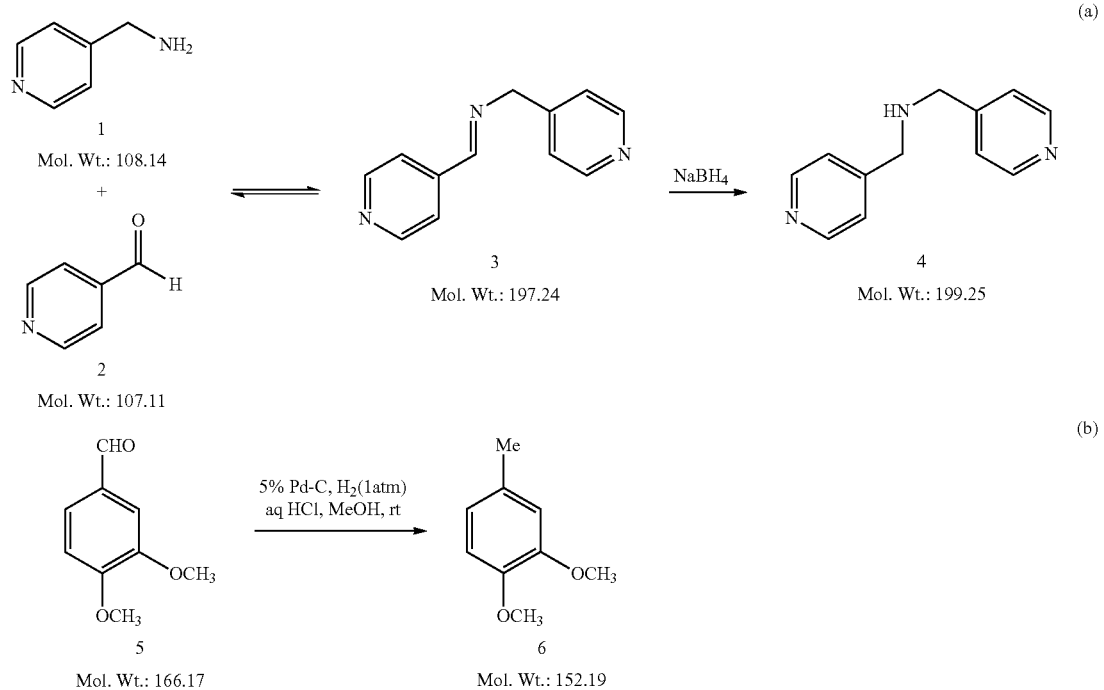

Apparatus for Inductive ESI-Based Reaction Monitoring

Figure 15:
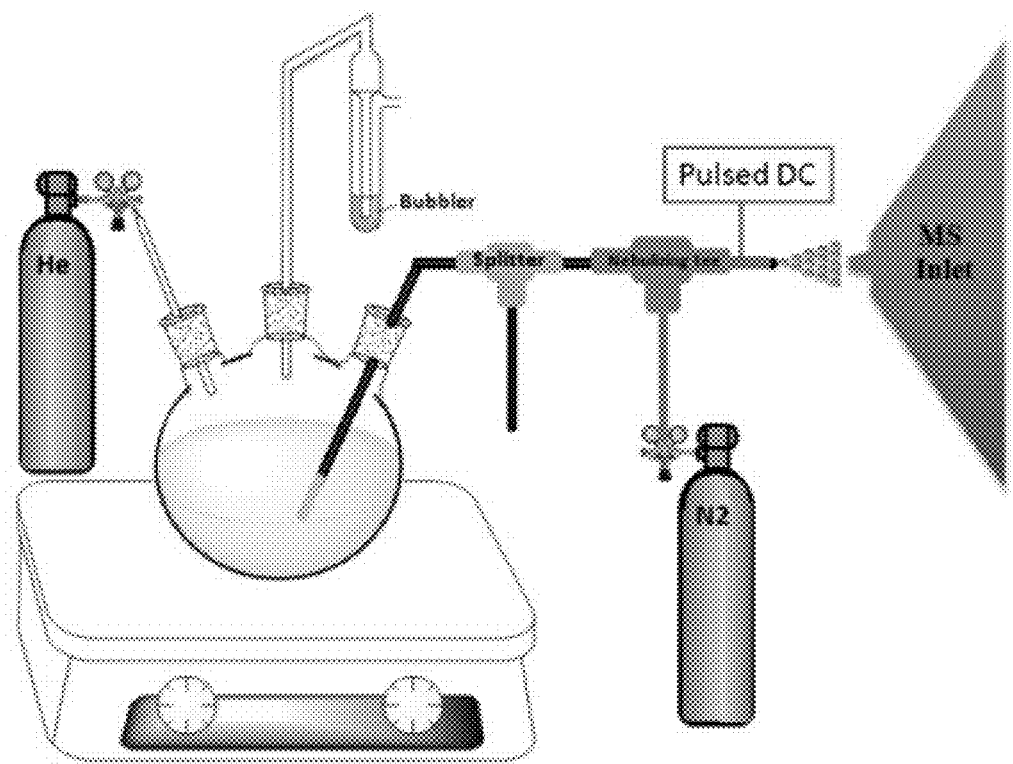
FIG. 15 is a schematic showing an inductive ESI-based on-line reaction monitoring system.

The configuration of the reaction monitoring system coupled with the inductive ESI ionization source is shown in FIG. 15. In a sealed three-neck reaction vessel, one end of a silica capillary (i.d. 100 µm, length 40 cm) was immersed into the reaction solution. Reaction solution was pressurized by helium (~5 psi) to allow transfer continuously through the capillary to the emitter-spray tip. A gas bubbler filled with a small amount of paraffin oil was used to monitor the isolation window of 1.5 Th (mass/charge units) and normalized collision energy of 30%-40% (manufacturer's unit) was selected for the CID experiments.

$^1$H NMR Spectroscopy

$^1$H NMR spectra were acquired using a Varian Inova-300 spectrometer (Department of Chemistry, Purdue University). Chemical shifts are reported in parts per million (ppm) using CD3OD as the reference peak.

Chemicals and Reagents

All reagents and solvents used were of analytical grade or higher and were used directly without further purification. 4-(Aminomethyl)pyridine, 4-pyridine-carboxaldehyde, sodium borohydride, 3,4-dimethoxy-benzaldehyde, palladium (5 wt. % on activated carbon) and HPLC grade methanol (MeOH) were purchased from Sigma-Aldrich (St. Louis, Mo., USA). Water was purified and deionized by a Milli-Q system (Millipore, Bedford, Mass., USA).

Synthesis of bis((pyridin-4-yl)methyl)amine (4) and Reaction Monitoring

To a three-neck round-bottom flask under He atm was added a solution of 1 (507 μL, 5 mmol) in 50 mL of MeOH, and then 2 (517 μL, 5.5 mmol) was injected. After stirring for 46 min, a solution of $NaBH_4$ (95 mg, 2.5 mmol) in 2 mL of H2O was injected to the reaction mixture. The resulting reaction mixture was stirred for 50 min. The whole reaction process was monitored by inductive ESI-MS which served to characterize intermediates and products.

Measurement of Delay Time

To a 50 mL of MeOH was injected 1 (507 μL, 5 mmol). The interval between injection of 1 into the solution and the time when the peak at m/z 109 was seen was recorded as the delay time. The whole process was monitored by inductive ESI-MS with capillary of different i.d. size and with or without a splitter.

Synthesis of 1,2-dimethoxy-4-methylbenzene (6) and Reaction Monitoring

The three-neck reaction flask used to monitor formation of 4 was equipped with a syringe filter on a syringe tube in the middle neck in order to prevent the Pd—C particles from blocking the capillary. The capillary for continuous sampling was inserted into the syringe tube and sucking the solution filtered. To a 46 mL of MeOH in the vessel was added 5% Pd—C (1.6 mg, 6 wt %). The air in the vessel was replaced by $H_2$. Instead of using a He cylinder, $H_2$ cylinder was used to provide $H_2$ continuously for hydrogenolysis. The precursor (5) (26 mg, 0.16 mmol) in 3 mL of MeOH was injected into the solution followed by adding aq HCl (1 μL) in 1 mL of MeOH. After 80 min, twice the amount of the Pd—C in methanol was added in small aliquots to the reaction mixture. The resulting reaction mixture was stirred for another 70 min. The whole reaction process was monitored by inductive ESI-MS.

Figure 16:
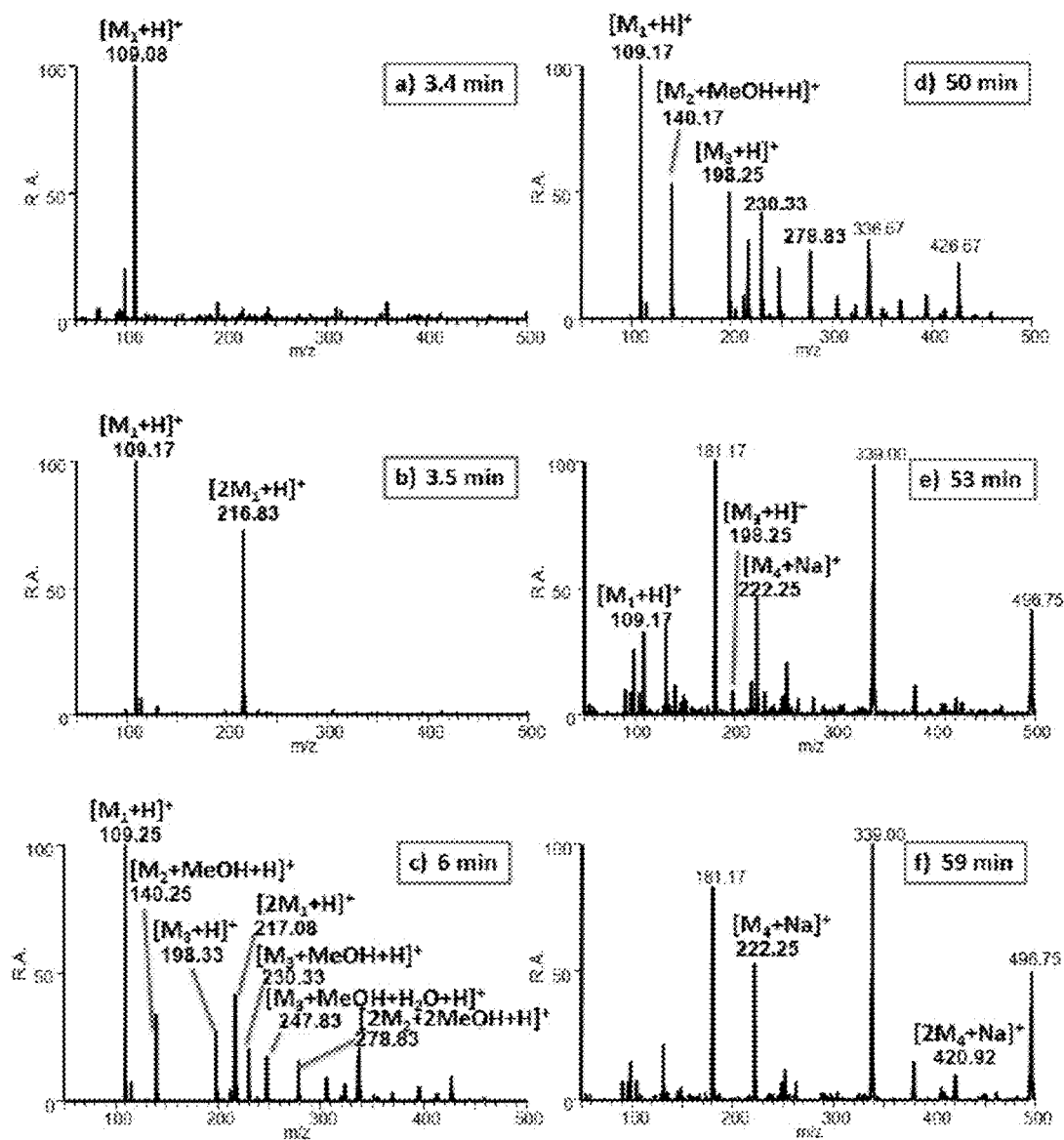
FIG. 16 panels A-F show time-resolved mass spectra of reductive amination of 4-pyridine-carboxaldehyde (2) with 4-(aminomethyl)pyridine (1). Reagent 1 was injected into the reaction solvent at 3 min.
Figure 17:
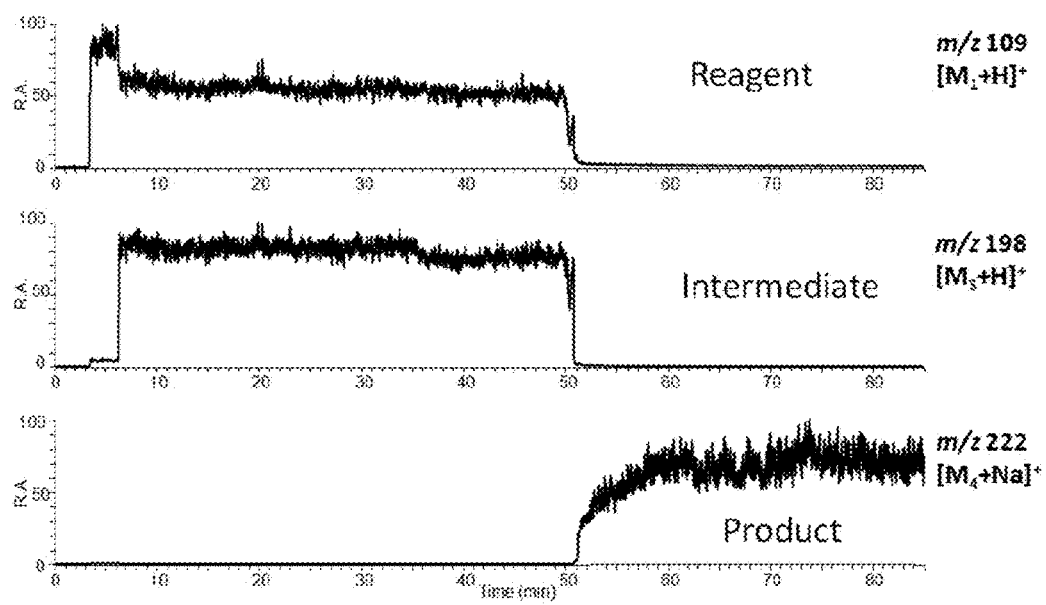
FIG. 17 is a selective ion chronogram showing protonated 1 disappearance, formation and disappearance of 3, and formation of 4 after NaBH$_4$ introduction.

On-Line Monitoring of Reductive Amination of 4-pyridine-carboxaldehyde with 4-(aminomethyl)pyridine In this Example, reductive amination of 4-pyridine-carboxaldehyde (2) with 4-(aminomethyl)pyridine (1) was carried out using a one-pot two-step protocol to produce bis((pyridin-4-yl)methyl)amine (4). Time-resolved mass spectra of the aldehyde-amine condensation step and the imine reduction step are shown in FIG. 16. Ions were identified according to their m/z values and confirmed by tandem mass experiment. Reactant 1 was first injected into the methanol reaction solvent. Ions of protonated 1 at m/z 109 were detected at 0.4 min later, on the heels of which the protonated dimer at m/z 217 appeared and reached its steady state within 4.8 s. (FIG. 16 panels A-B) After reactant 2 was injected into the reaction solution and the protonated methanol adduct ions of the monomer and dimer of 2 at m/z 140 and 279 showed up. The ions of the intermediate (pyridin-4-yl)-N-((pyridin-4-yl)methylene)methanamine (3) at m/z 198 and 230 formed quickly and the intensity increased sharply (FIG. 16 panel C). The intensity of ions of 1 decreased but the ions did not disappear, which corresponded to the fact that this is an equilibrium reaction (FIG. 16 panel D). About 50 min later, sodium borohydride solution was injected into the system. The sodiated adduct ions of product 4 at m/z 222 started to appear, while the intermediate ions of 3 decreased a lot (FIG. 16 panel E). Ten minutes later, the peak of the product 4 was reaching its highest intensity (FIG. 16 panel F). The selected ion chronogram shows dynamic changing of ions corresponding to the precursor 1, intermediate 3 and product 4 (FIG. 17). The kinetic process of reductive amination can be clearly seen. The first condensation step of this reaction happened very fast; once 2 was added to the solution of 1, it took less than 1 min for the reaction to reach equilibrium. The intermediate 3 was generated simultaneously with the decrease of 1. The second reduction step was not as fast as the first step. With the reduction of intermediate 3, the first step was driven to the right. Thus ions of 1 were depleted. Altogether, it took around 10 min for the product 4 to reach its highest intensity. The total monitoring time was 90 min without any clogging in the fused-silica capillary using high concentrations of reaction solution that are representative of those of industrial interest.

Figure 18:
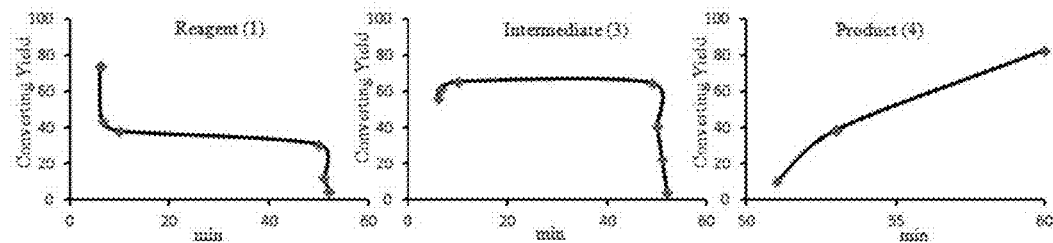
FIG. 18 is a set of graphs showing kinetic curves of compounds 1, 3, 4 in reductive amination of 4-pyridine-carboxaldehyde with 4-(aminomethyl)pyridine monitored by $^1$H NMR.

The above kinetic data obtained by inductive ESI-MS monitoring were compared to that collected through $^1H$ NMR monitoring to verify the accuracy. Reductive amination of 2 with 1 was studied under the same conditions but monitored by $^1H$ NMR. Because the reaction cannot be monitored continuously, we chose several time points and sampled aliquots of the solution for NMR analysis. Hydrogens from the methylene groups in compounds 1, 3, 4 have different chemical shifts (4.8 ppm, 5.5 ppm and 4.6 ppm, respectively) due to the differences in the adjacent N-containing functional groups. Therefore the hydrogen signals of the methylene groups were chosen as the characteristic marker for each compound. The product yield at each selected time point was calculated as the ratio of methylene peak area for compound 4 vs the total for 1, 3 and 4. The yield is shown as a kinetic curve in FIG. 18. Comparing the kinetic curves obtained by inductive ESI-MS and $^1H$ NMR, the same time trends are shown. The kinetic data acquired by inductive ESI-MS provided continuous and more detailed information of the reaction. The reaction selected here was relatively simple; in other reactions there might be more than four main compounds. This would represent a challenge for $^1H$ NMR owing to the difficult peak assignments in mixture, while even in that case each selected ion chronogram could be still obtained from MS.

The time lag between sampling and measuring compounds in a reaction mixture, is an important factor that should be taken into account in reaction monitoring, because it affects accuracy of kinetic data and determines how quickly the operator can respond to an unexpected situation. In off-line MS reaction monitoring, delay time emerging from sampling, sample preparation and analysis process is various, uncontrollable and always lengthy. In on-line MS reaction monitoring, the sample is transferred directly from the reaction system to the MS. The MS result thus represents the state of the reaction system continuously with a short offset for solution transport which is often done by a capillary. Under certain vessel pressure, the length and the inner diameter of the chosen capillary determines the duration time of the delay, which reduces uncertainty of measuring the delay time.

Figure 19:
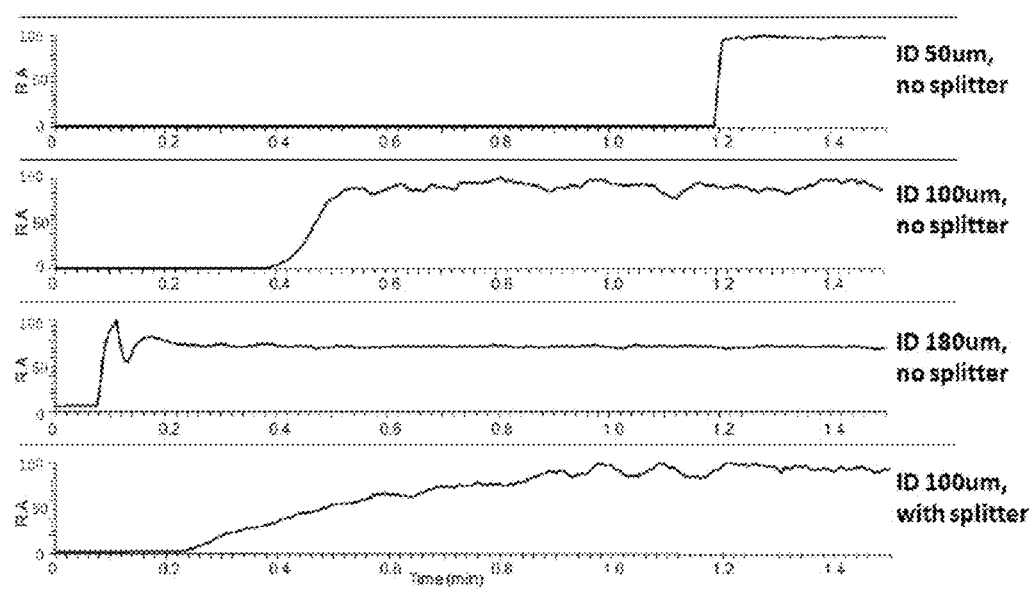
FIG. 19 shows a selected ion chronogram of 4-(aminomethyl)pyridine (1) when measuring the delay time of inductive ESI-MS monitoring system.

In this Example, delay time of inductive ESI-MS monitoring system was measured using capillaries of various inner diameters but the same length (40 cm). The selected ion chronogram of ions of 1 illustrates the delay time after reagent addition (FIG. 19). The delay time for i.d. 50 μm is 1.2 min and this was decreased to 2.4 s when using a capillary of i.d. 180 μm. In this case, however, the consumption of the reaction solution for electrospray was as high as 0.19 mL/min. The large spray volume of analytes could contaminate the MS inlet. In order to decrease the amount of analytes into MS while maintain the short delay time, a three-way sample splitter was added before the nebulizing gas tee. A capillary with double the inner diameter (i.d. 200 μm) was used for the splitter outlet that accelerated the replacement of solution inside the transferring capillary. The arrival time in the splitter equipped system was 0.2 min faster than that without a splitter tee. Thus, the flow rate of sampling was increased, while the volume of solution used for ionization in the emitter was still kept the same as that delivered by a 100 μm capillary which effectively avoided contamination of MS inlet.

On-Line Monitoring of Pd—C Catalyzed Hydrogenolysis of 3,4-dimethoxy-benzaldehyde Pd—C catalyzed hydrogenation has been widely employed in numerous organic transformations (Merz et al., M. Synthesis 1993, 797-802; and Sagar et al., Bioorg. Med. Chem. 2004, 12, 4045-4054). The reaction commonly proceeds under $H_2$ atmosphere, which requires the reaction system pressure-tight or within a positive pressure of $H_2$. So far, almost no available MS monitoring system is possible for monitoring this type of reaction. Inductive ESI-MS reaction monitoring is using a sealed flask with positive pressure inside, which is able to expand the scope to monitoring reaction involving gas as a reactant or reactants sensitive to air and water. Here, Pd—C catalyzed hydrogenolysis of 3,4-dimethoxybenzaldehyde was chosen to be monitored by inductive ESI-MS.

Figure 20:
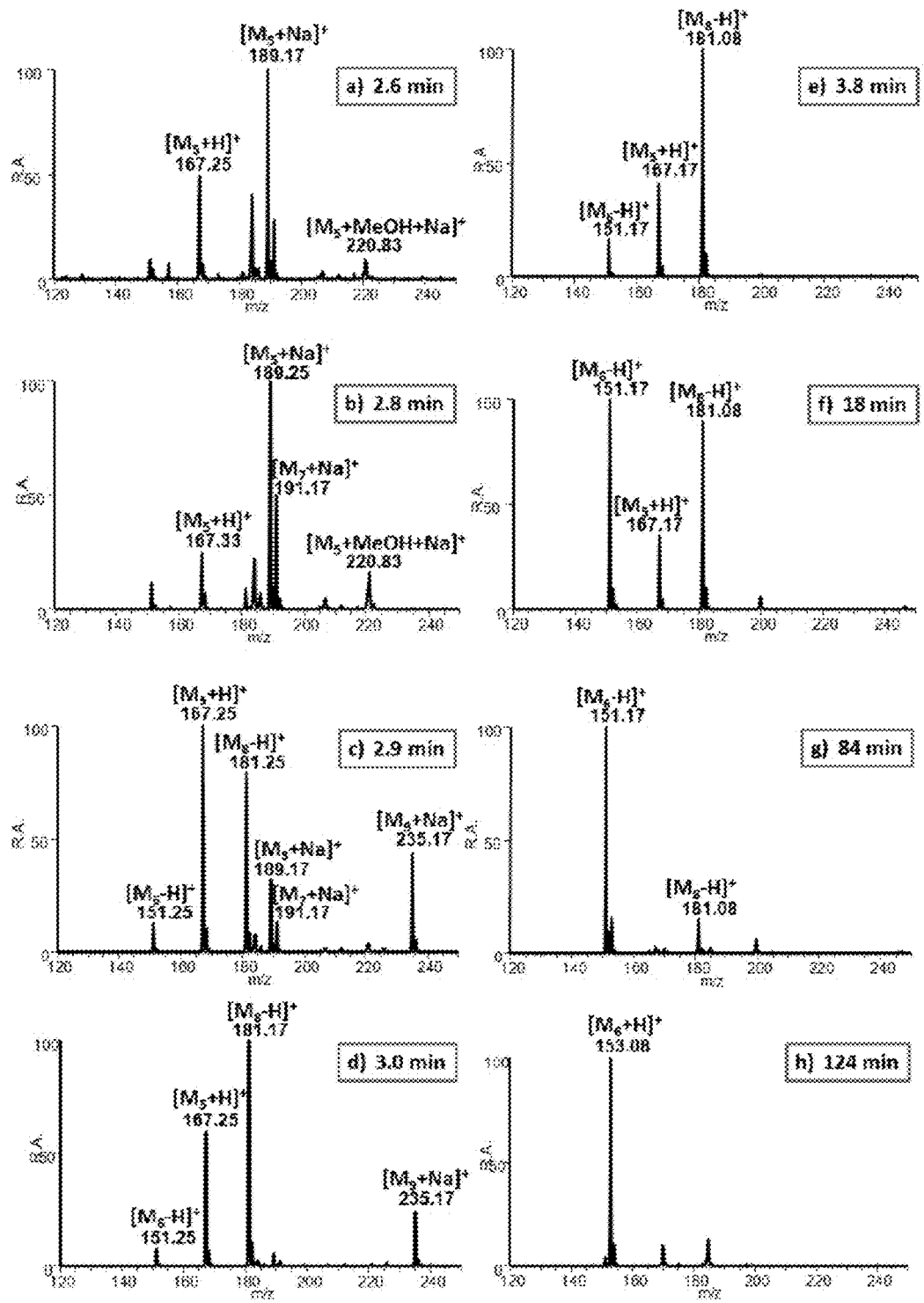
FIG. 20 panels A-H show time-resolved mass spectra of Pd—C catalyzed hydrogenolysis of benzaldehydes reaction mixture. Precursor 5 was injected into the suspension of Pd/C in methanol at 2 min.

Time-resolved mass spectra of Pd—C catalyzed hydrogenolysis of 3,4-dimethoxybenzaldehyde are shown in FIG. 20. Ions were determined based on their m/z values and tandem MS. At 0.48 min after precursor 5 was injected into the Pd/C suspension of methanol, its ions $[M_5+H]^+$ at m/z 167 and $[M_5+Na]^+$ at m/z 189 were detected and the reaction started (FIG. 20, panel A). Within 0.02 min, a new peak at m/z 191 started to appear. It reached its highest intensity within 0.4 min and disappeared 0.15 min later (FIG. 20, panel B). Another two new peaks at m/z 235 and 181 was shown 0.34 min and 0.38 min behind the peak at m/z 191 respectively (FIG. 20, panel C-D). 0.3 min later, the peak at m/z 235 disappeared while the peak at m/z 181 dominated the reaction (FIG. 20, panel E-F). At the same time, the ion of hydrogenolysis product 6 at m/z 151 began to form. It became base peak at 18 min, and dominated the reaction at 45 min (FIG. 20, panel G). The whole reaction process showed there were three intermediates (m/z 191, 235 and 181) produced before the formation of the hydrogenolysis product.

Figure 21A:
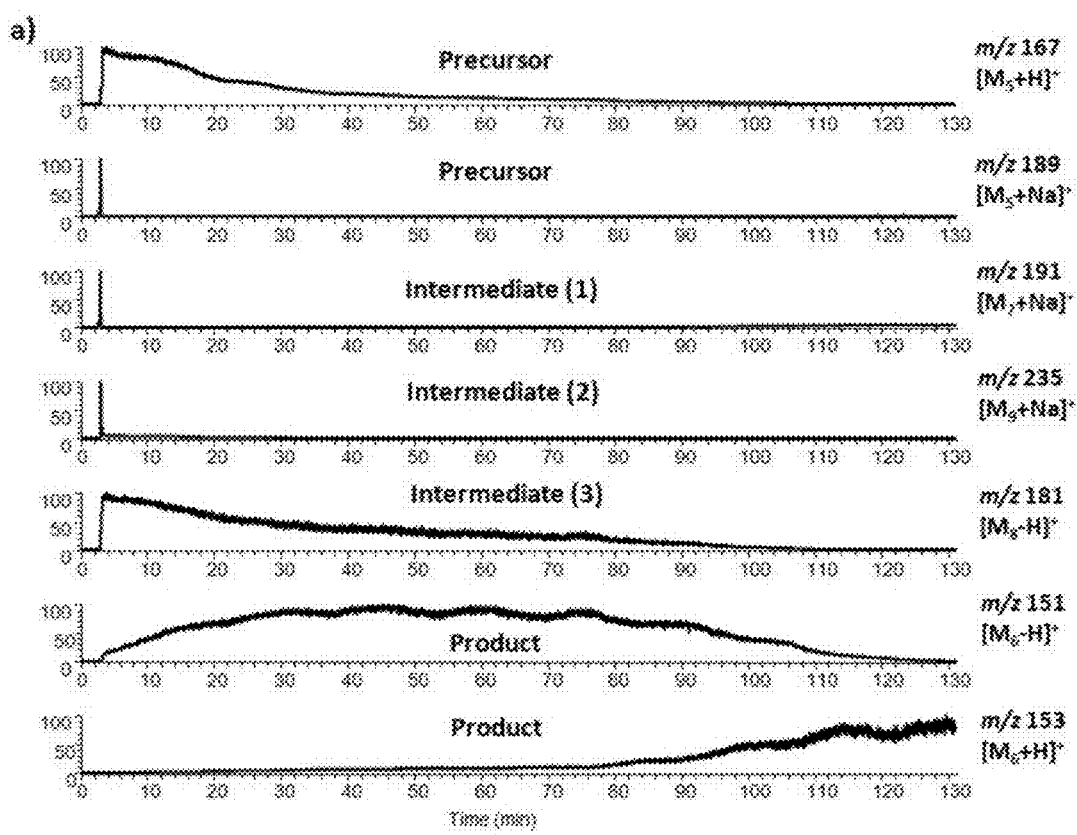
FIGS. 21A-B show a selective ion chronogram of the precursor 5, intermediate 7, 8, 9 and product 6 in the reaction of Pd—C catalyzed hydrogenolysis of 3,4-dimethoxy-benzaldehyde.
Figure 21B:
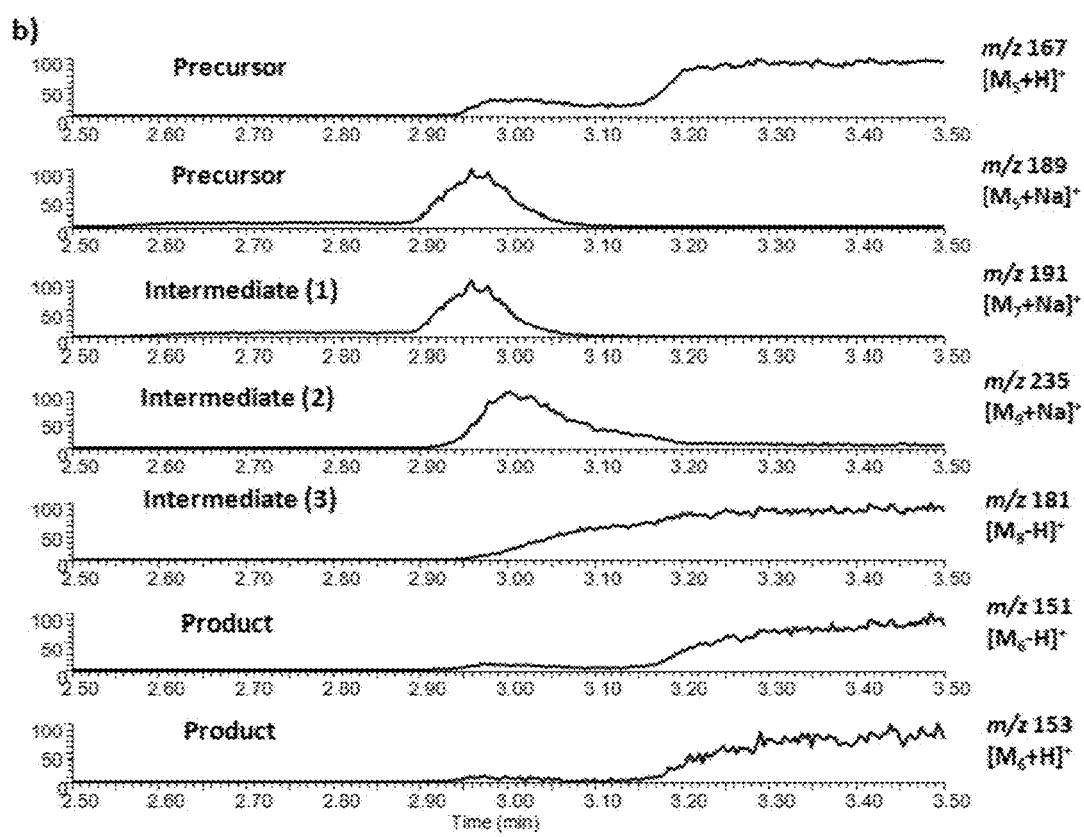

The trap of transient intermediates in the Example of reaction mechanism is significantly important, while their short lives challenge the classic way of monitoring reaction such as TLC, HPLC and GC which requires a certain time for analysis. Online inductive ESI-MS monitors the reaction continuously and provides instant structure information for all of the analytes in the mixture solution, therefore it has the capability to catch the transient intermediates. The kinetics of Pd—C catalyzed hydrogenolysis of benzaldehydes in methanol was provided in FIGS. 21A-B, showing changing curves of ions corresponding to the precursor 5, three intermediates 7, 8, 9, and the product 6. From selected ion chronogram at time range of 2.5-3.5 min (FIG. 21B), the intermediate ion at m/z 191 was formed firstly among the three intermediates and almost at the same time when the precursor 5 was added. The appearance of its peak centralized in 2.9-3.05 min. The intermediate ion at m/z 235 was shown followed by m/z 191 and appeared 93% of its peak area in 2.9-3.2 min. The life time of these two intermediates was as short as less than 0.3 min. With the decrease of the former intermediates, the intermediate ion at m/z 181 increased, by the conversion of which the product 6 was finally formed.

Pd—C catalyzed hydrogenolysis of benzaldehydes to methylbenzenes has been described as proceeding via benzenemethanol intermediate pathway (Nishimura et al., S. Handbook of heterogeneous Catalytic Hydrogenation for Organic Synthesis; John Wiley & Sons: New York, N.Y., 2001; Chapter 5; Connolly et al., J. Med. Chem. 1996, 39, 46-55) because benzenemethanol was often isolated as an intermediate or as a major by-product. In the above case, intermediate ions at m/z 191, 235 and 181 were assigned as sodiated adduct ions of dimethoxy benzenemethanol (7), sodiated adduct ions of dimethoxy benzaldehyde dimethyl acetal (9) and hydride abstraction ions of dimethoxy benzyl methyl ether (8), respectively. In agreement with the classic benzenemethanol pathway, 3,4-Dimethoxybenzaldehyde was firstly hydrogenated to dimethoxy benzenemethanol (m/z 191), then converted to dimethoxy benzyl methyl ether (m/z 181), and finally dimethoxy toluene (m/z 151) was produced. However, this could not explain the appearance of dimethoxy benzaldehyde dimethyl acetal (m/z 235). The observed sodiated adduct ions dimethoxy benzaldehyde dimethyl acetal suggested a second new pathway of hydrogenolysis where benzaldehyde acetal was produced as an intermediate instead of benzenemethanol. Recently, the similar benzylaldehyde acetal intermediate was separated and confirmed (Merz et al., Synthesis 1993, 797-802). Although, that work claimed that when lower alcohols (methanol or ethanol) were used as solvents, only benzylaldehyde acetal intermediate rather than benzenemethanol was produced as the first intermediate. Instead, a new two-way three-stage pathway involving three intermediates 7, 8, 9 was proposed here as shown in scheme 2, by which the functions of each reaction intermediate were well recognized.

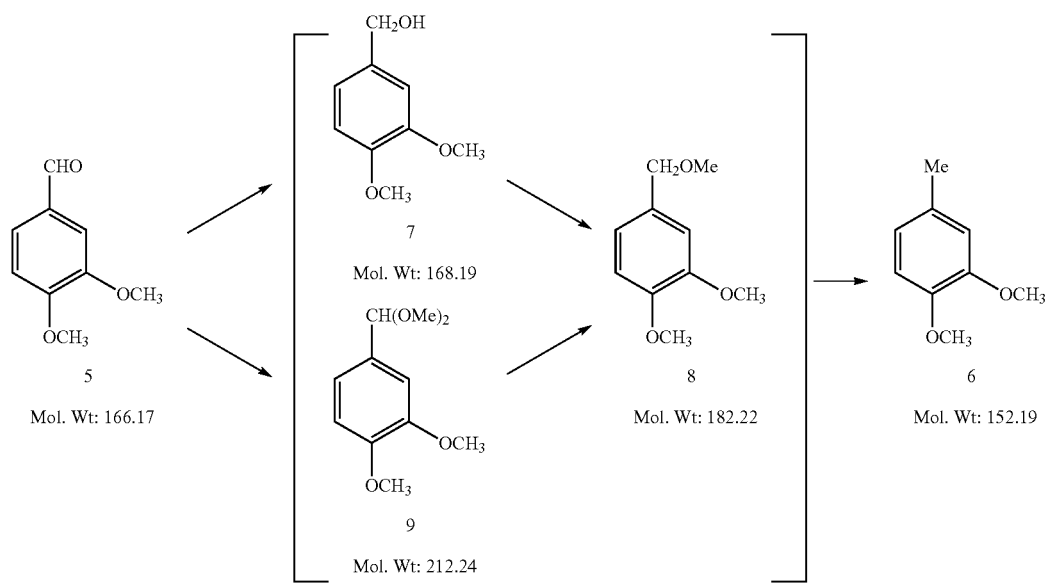

The observed cations at m/z 181 and 151 were one mass unit lower than the molecular weight of compound 8 and 6 respectively, and so correspond to loss of hydride from the neutral molecules. The key step in ESI is normally the generation of the protonated form of the molecule: M+ AH$^+$→[M+H]$^+$+A. However, hydride abstraction is well known route to positive ion formation in chemical ionization mass spectrometry. It is possible the presence of trace Pd/C particles affect the outcome of the encounter between a proton donor and a molecule in the present ESI experiments favoring hydride loss by providing a route to H$_2$ take up as discussed later.

When Pd—C catalyzed hydrogenolysis of 3,4-dimethoxybenzaldehyde in methanol was studied for the first time, the reaction was stopped when ions at m/z 151 dominated the reaction (FIG. 20 panel G). However, when the reaction mixture was kept overnight and re-examined by inductive ESI-MS again the next morning, the peak at m/z 151 had almost disappeared, being replaced by a peak at m/z 153. In order to determine whether they were the different compounds or the same ones subjected to different ionization methods, two reaction mixtures were prepared for $^1$H NMR, one dominated by the ions at m/z 151 and the other dominated by the ions at m/z 153, respectively. The $^1$H NMR results confirmed the formation of the same product 6. Therefore m/z 151 was assigned to [M−H]$^+$, while m/z 153 represents [M+H]$^+$. In order to explore the relationship of these two ionized forms of what is apparently the same neutral product, the kinetics was monitored continuously (FIG. 20 panel A). After 80 min, twice the initial amount of Pd/C in methanol was added to the reaction mixture. At 120 min, the ions at m/z 153 finally became the dominant peak (FIG. 20 panel H). During the long time interval when the peak at m/z 151 was decreasing and that at m/z 153 was increasing, the two peaks displayed a one-to-one correspondence, which again suggested they were generated from the same compound. We speculate that as intermediate 8 was consumed and converted to product 6, there remained no substrates for hydrogenation in the system. The surface of the Pd/C then became saturated with H$_2$ which eliminated the driving force of hydride abstraction. The formation of the protonated rather than the deprotonated form of the product occurred and dominated the mixture in the end.

Conclusions

Inductive ESI-MS was a useful tool for direct and continuous monitoring of organic reactions in situ while avoiding any need for physical contact of the high voltage with the reaction solution. Sheath gas was used to help in the nebulization process and minimize size-variation in the droplets. Sample splitting was useful in accelerating flow rate of sampling and decreasing the delay time while avoiding contamination of the MS inlet. The kinetic study of reductive amination monitored by inductive ESI-MS compared well with that acquired off-line by $^1$H NMR, which verified that inductive ESI-MS reaction monitoring system reflected the dynamic trend of the reaction. It also provided more detailed information than $^1$H NMR. Online monitoring Pd—C catalyzed hydrogenolysis of 3,4-dimethoxy benzaldehydes was successfully monitored in the sealed vessel with positive H$_2$ supplying system. Hydride abstraction ion [M−H]$^+$ was observed in Pd/C involved reaction and possible reasons were provided.

On-line monitoring of the reaction by inductive ESI-MS permitted the monitoring of how the reaction proceeded, and allowed for the detection and characterization of the transient reaction intermediates, which provides a general and efficient way to investigate the reaction mechanism. The system is applicable to reactions that are sensitive to air or water. Moreover, since inductive ESI has been proved to facilitate high throughput detection, the system has the possibility to monitor several parallel reactions at the same time by multiplexing reactions and analyzing with a single mass spectrometer.

Example 3: Solvent Compatibility

In on-line reaction monitoring, the solvent used for conducting the reaction is directly flowed to an ion generating device for production of the ions that are analyzed in real-time. Therefore, in on-line reaction monitoring, the reaction solvent is also the ionization solvent. Importantly, the solvent used in on-line reaction monitoring must be compatible as both the reaction solvent and the ionization solvent for on-line reaction monitoring to work. Choosing a reaction solvent that is not capable of also being an ionization solvent results in an inability to generate ions of reaction intermediates and final products in real-time. On the other hand, choosing a reaction solvent that works well for ionization, but is not compatible with the reaction to be conducted results in an inability to conduct the reaction. This aspect of the invention is exemplified below.

The Negishi reaction, palladium-catalyzed cross-coupling of organohalides with organozinc reagents, is a selective and versatile method for the formation of C—C bonds that has been widely used in fields ranging from medicine to agriculture and materials development. The reagents involved in the Negishi reaction are extremely susceptible to the presence of water or oxygen, as a result the reaction needs to be performed with strict exclusion of water and air. This represents a challenge to any on-line monitoring system. Due to that difficulty, on-line reaction monitoring has not been used for any air and/or water sensitive reactions. The Negishi reaction is also of interest because of a series of cascaded reaction intermediates, the instability and transience of which prevents their isolation and purification. Mass spectrometry is especially suitable for following the rapid transformations of the intermediates without separation.

In this Example, cross coupling of 3-bromoquinoline with diethyl zinc catalyzed by Pd-PEPPSI (palladium-pyridine, enhanced precatalyst, preparation, stabilization and initiation) in tetrahydrofuran (Scheme 1) was monitored by inductive ESI-MS.

Scheme 1: Negishi cross coupling of 3-bromoquinoline with diethyl zinc catalyzed by Pd-PEPPSI (palladium-pyridine, enhanced precatalyst, preparation, stabilization and initiation) in tetrahydrofuran

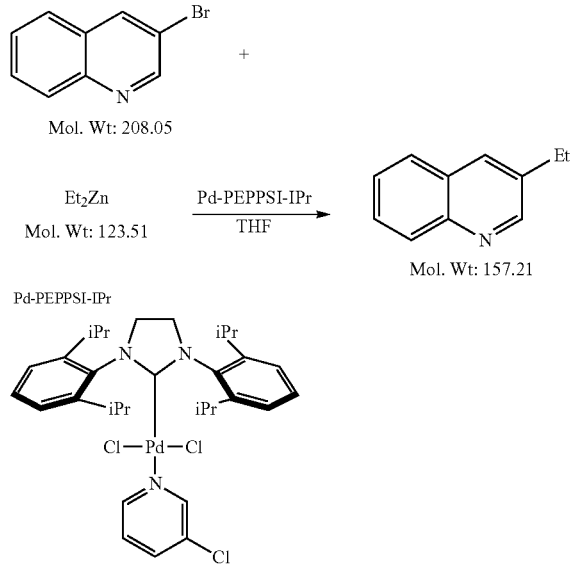

Figure 22:
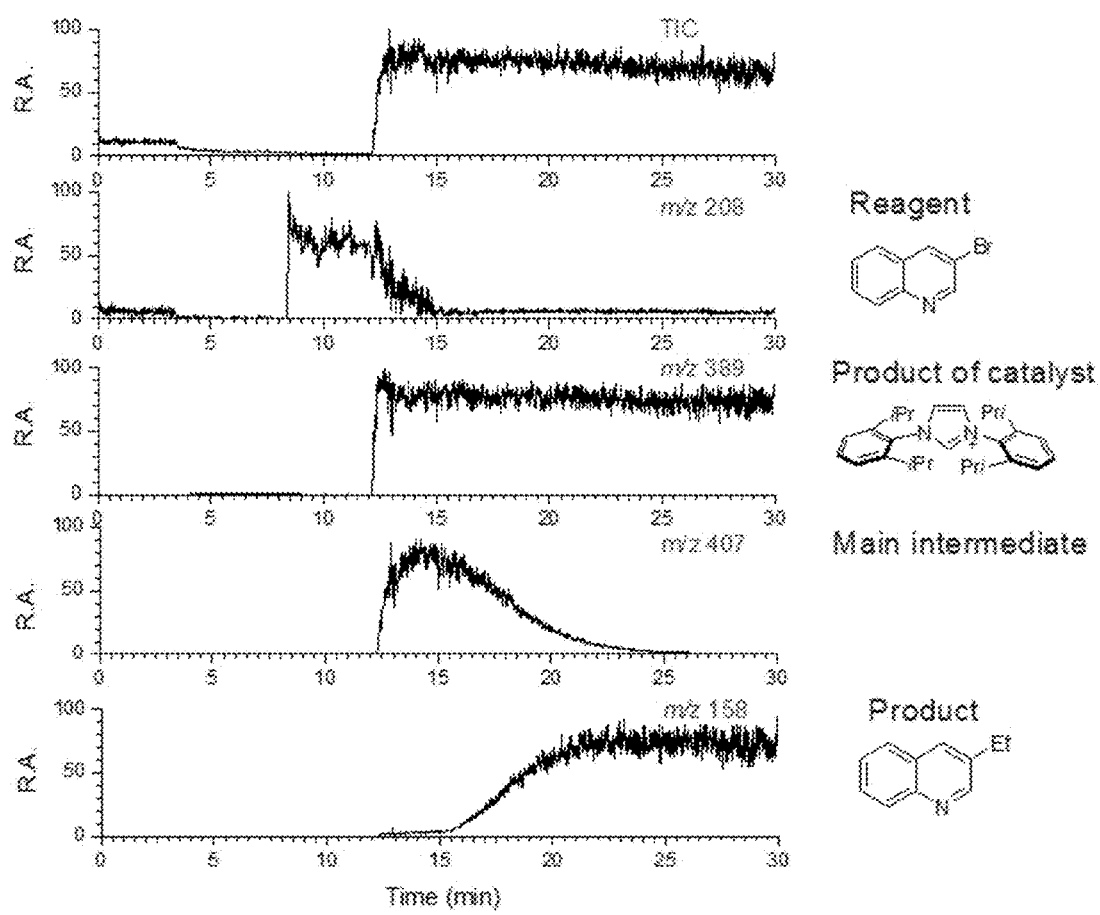
FIG. 22 is a total ion chronogram and selective ion chronograms showing 3-bromoquinoline (m/z 208), the product of Pd-PEPPSI (m/z 389), a representative intermediate (m/z 407) and the reaction product ethylquinoline (m/z 158) in the Negishi cross coupling of 3-bromoquinoline with diethyl zinc catalyzed by Pd-PEPPSI in THF using the inductive ESI apparatus described herein.
Figure 23:
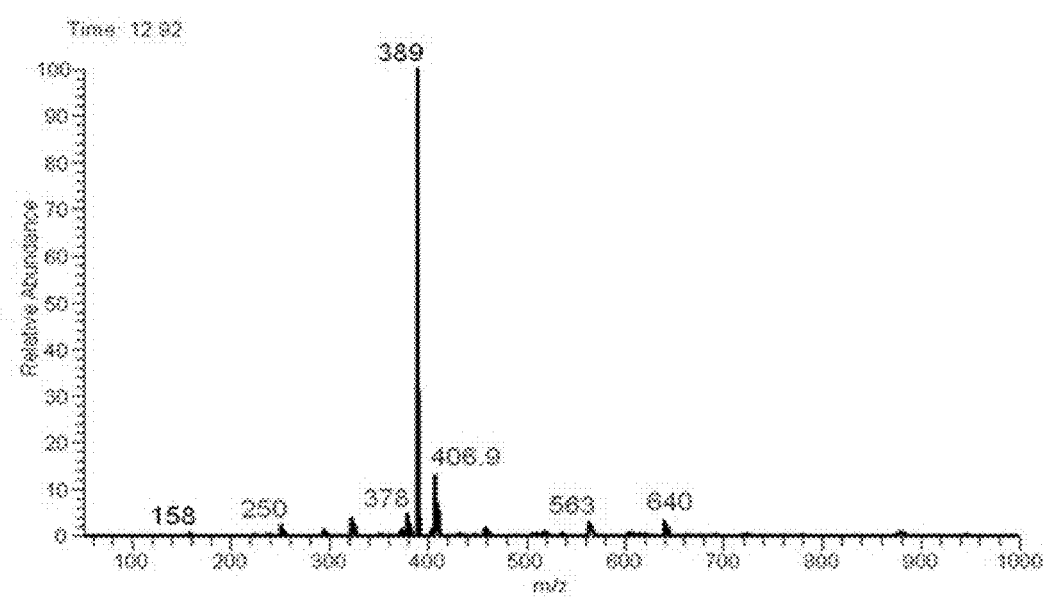
FIG. 23 is an inductive ESI mass spectrum of the Negishi cross coupling reaction mixture of 3-bromoquinoline with diethylzinc catalyzed by Pd-PEPPSI in THF recorded at 12.92 min.

The kinetics of the Negishi cross coupling is shown in FIG. 22, in which the changing abundances of the total ion current, and the currents corresponding to the 3-bromoquinoline (m/z 208), the Pd-PEPPSI product (m/z 389), a representative intermediate (m/z 407) and the reaction product ethylquinoline (m/z 158) are displayed. At 8.4 min after 3-bromoquinoline was injected into a solution of catalyst Pd-PEPPSI, the protonated ions of 3-bromoquinoline at m/z 208 and 210 were detected. With the injection of diethyl zinc reagent over the period 11.6-14 min, catalyst Pd-PEPPSI was activated from Pd (II) to Pd (0) and ions at m/z 389 derived from the ligated N-heterocyclic carbine showed up at 12.2 min. Protonated 3-bromoquinoline began to decrease at 12 min, while several reaction intermediates were detected including major ions at m/z 407, 379 and 250 (FIG. 23) before the reaction product ions due to protonated ethylquinoline at m/z 158 gained their sharp increase. The intermediates began to decrease at 15 min and at the same time the reaction product ethylquinoline increased steadily and reach its highest intensity at 22 min.

In the online monitoring system for this reaction, the reaction solvent also serves as the spray solvent in order to exclude air and moisture and avoid introduction of interference of unnecessary ions. When using spray-based ionization methods, the chosen solvent has an effect on the ionization performance of an analyte of interest, which may be attributed to the properties of the solvent including surface tension, solvent polarity and vapor pressure. In this Example, anhydrous tetrahydrofuran (THF) was used as the reaction and spray solvent for online reaction monitoring.

Without consideration for the reaction, methanol or methanol/water mixture would be best for ionization. However, those solvents would not be compatible as reaction solvents. Using the same setup as in this Example, methanol and methanol/water were used as solvents for online monitoring of a Negishi reaction. It was found that the intensity, continuity and stability of recorded MS signal were much worse.

What is claimed is:

1. An online reaction monitoring system, the system comprising:
    a reaction vessel comprising an outlet port;
    a channel that extends from within the outlet port;
    an electrode operably associated with a distal end of the channel, wherein the electrode is external to the channel and does not physically contact the channel or a liquid or vapor within the channel; and
    a mass spectrometer.

2. The system according to claim 1, wherein the electrode is positioned to inductively interact with a distal end of the channel.

3. The system according to claim 1, wherein the reaction vessel comprises one or more inlet ports.

4. The system according to claim 3, wherein the system further comprises a gas source operably coupled to the reaction vessel through one of the one or more inlet ports.

5. The system according to claim 1, wherein the channel extends into the reaction vessel.

6. The system according to claim 1, wherein the channel comprises one or more splitters.

7. The system according to claim 6, wherein a first splitter withdraws a portion of a liquid from the channel.

8. The system according to claim 7, wherein a second splitter is coupled to a nebulizing gas source in order to introduce a nebulizing gas into the channel.

9. The system according to claim 1, further comprising a heating element operably associated with the reaction vessel.

10. The system according to claim 1, wherein the mass spectrometer is a miniature mass spectrometer.

11. An online reaction monitoring system, the system comprising:
    a reaction vessel comprising an outlet port;
    a channel that extends from within the outlet port;
    an electrode positioned to inductively interact with a distal end of the channel, wherein the electrode is external to the channel and does not physically contact the channel or a liquid or vapor within the channel and the electrode produces a pulsed current; and a mass spectrometer.

12. The system according to claim 11, wherein the pulsed current is a pulsed DC current.

13. The system according to claim 11, wherein the reaction vessel comprises one or more inlet ports.

14. The system according to claim 13, wherein the system further comprises a gas source operably coupled to the reaction vessel through one of the one or more inlet ports.

15. The system according to claim 11, wherein the channel extends into the reaction vessel.

16. The system according to claim 11, wherein the channel comprises one or more splitters.

17. The system according to claim 16, wherein a first splitter withdraws a portion of a liquid from the channel.

18. The system according to claim 17, wherein a second splitter is coupled to a nebulizing gas source in order to introduce a nebulizing gas into the channel.

19. The system according to claim 11, further comprising a heating element operably associated with the reaction vessel.

20. The system according to claim 11, wherein the mass spectrometer is a miniature mass spectrometer.

* * * * *